US012637452B2

(12) United States Patent
Garceau et al.

(10) Patent No.: US 12,637,452 B2
(45) Date of Patent: May 26, 2026

(54) CRYSTALLINE FORMS OF A SUBSTITUTED IMIDAZOPYRIDINE COMPOUND AND USE THEREOF AS P2X3 MODULATOR

(71) Applicant: GlaxoSmithKline Intellectual Property (No. 3) Limited, Stevenage (GB)

(72) Inventors: Denis Garceau, Laval (CA); Robert M. Wenslow, Jr., Laval (CA); Kemal Payza, Laval (CA); Nathalie Chauret, Laval (CA)

(73) Assignee: GlaxoSmithKline Intellectual Property (No.3) Limited, Stevenage (GB)

(*) Notice: Subject to any disclaimer, the term of this patent is extended or adjusted under 35 U.S.C. 154(b) by 1124 days.

(21) Appl. No.: 17/292,663

(22) PCT Filed: Nov. 12, 2019

(86) PCT No.: PCT/IB2019/001199

§ 371 (c)(1),
(2) Date: May 10, 2021

(87) PCT Pub. No.: WO2020/099923

PCT Pub. Date: May 22, 2020

(65) Prior Publication Data

US 2022/0002292 A1 Jan. 6, 2022

Related U.S. Application Data

(60) Provisional application No. 62/760,307, filed on Nov. 13, 2018.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC ... C07D 471/04; C07B 2200/13; A61P 11/14; A61P 13/00; A61P 15/00; A61P 29/00; A61P 17/04; A61K 31/5377
See application file for complete search history.

(56) References Cited

U.S. PATENT DOCUMENTS

| | | | | |
|---|---|---|---|---|
| 6,673,908 | B1 * | 1/2004 | Stanton, Jr. | C07K 14/7151 435/6.16 |
| 7,550,495 | B2 | 6/2009 | Page et al. | |
| 8,530,467 | B2 | 9/2013 | Cantin et al. | |
| 9,598,409 | B2 * | 3/2017 | Buon | A61P 13/00 |
| 9,814,725 | B2 | 11/2017 | Buon et al. | |
| 9,937,815 | B2 | 4/2018 | Smidebrant et al. | |
| 10,111,883 | B1 * | 10/2018 | Garceau | A61K 31/437 |
| 2003/0124028 | A1 * | 7/2003 | Carlson | C40B 60/14 422/68.1 |
| 2006/0264490 | A1 | 11/2006 | Page et al. | |
| 2015/0290181 | A1 | 10/2015 | Lee et al. | |
| 2015/0361078 | A1 | 12/2015 | Buon et al. | |
| 2017/0143730 | A1 | 5/2017 | Buon et al. | |
| 2017/0326141 | A1 | 11/2017 | Trower | |
| 2018/0015099 | A1 | 1/2018 | Buon et al. | |
| 2019/0300957 | A1 | 10/2019 | Gonsky et al. | |
| 2020/0390779 | A1 | 12/2020 | Buon et al. | |
| 2021/0228588 | A1 | 7/2021 | Buon et al. | |
| 2021/0322432 | A1 | 10/2021 | Garceau et al. | |
| 2021/0346391 | A1 | 11/2021 | Matzouranis et al. | |
| 2021/0386751 | A1 | 12/2021 | Matzouranis et al. | |
| 2023/0101612 | A1 | 3/2023 | Chauret et al. | |

FOREIGN PATENT DOCUMENTS

| | | | |
|---|---|---|---|
| CA | 921395 | A | 2/1973 |
| CA | 2655780 | A1 | 12/2007 |
| CA | 2777746 | A1 | 5/2011 |

(Continued)

OTHER PUBLICATIONS

Hurst et al., Analytica Chimica Acta, 337 (1997), 233-52 (Year: 1997).*

Campbell Roberts et al., J. Pharm. Biomed. Anal., 28 (2002) 1149-59 (Year: 2002).*

Tiwari et al., J. Pharm. Biomed. Anal., 43 (2007) 865-72 (Year: 2007).*

Strachan, C.J., Rades, T., Gordon, K.C. and Rantanen, J. (2007), Raman spectroscopy for quantitative analysis of pharmaceutical solids. Journal of Pharmacy and Pharmacology, 59: 179-192. https://doi.org/10.1211/jpp.59.2.0005 (Year: 2007).*

F. Sáez-Orellana et al. / Pharmacological Research 101 (2015) 109-115 (Year: 2015).*

(Continued)

*Primary Examiner* — James H Alstrum-Acevedo
*Assistant Examiner* — Chantal Adlam
(74) *Attorney, Agent, or Firm* — William B. Stauffer

(57) ABSTRACT

Described herein are crystalline forms of a P2X3 modulator, namely (S)-methyl-2-((2-(2,6-difluoro-4-(methylcarbamoyl)phenyl-7-methylimidazo[1,2-a]pyridin-3-yl)methyl) morpholine-4-carboxylate or a solvate thereof, and use thereof for treating pain, urinary tract disorder, cough, pruritus and endometriosis.

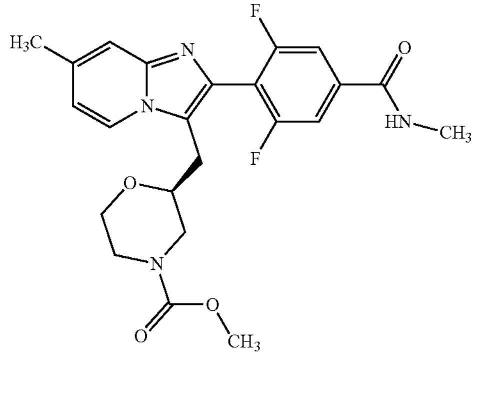

4 Claims, 11 Drawing Sheets

(56) References Cited

FOREIGN PATENT DOCUMENTS

| | | | |
|---|---|---|---|
| CA | 2898665 | A1 | 8/2014 |
| CA | 2921395 | A1 | 2/2015 |
| CA | 2998742 | A1 | 4/2017 |
| CN | 102741245 | A | 10/2012 |
| EP | 0533266 | A1 | 3/1993 |
| EP | 2501697 | A1 | 9/2012 |
| JP | 2004002826 | A | 1/2004 |
| RU | 2294935 | C2 | 3/2007 |
| WO | WO-9722596 | A1 | 6/1997 |
| WO | WO-9730035 | A1 | 8/1997 |
| WO | WO-9732856 | A1 | 9/1997 |
| WO | WO-9813354 | A1 | 4/1998 |
| WO | WO-9902166 | A1 | 1/1999 |
| WO | WO-0040529 | A1 | 7/2000 |
| WO | WO-0041669 | A2 | 7/2000 |
| WO | WO-0047212 | A1 | 8/2000 |
| WO | WO-0192224 | A1 | 12/2001 |
| WO | WO-0194341 | A1 | 12/2001 |
| WO | WO-0204434 | A1 | 1/2002 |
| WO | WO-0208213 | A1 | 1/2002 |
| WO | WO-02085309 | A2 | 10/2002 |
| WO | WO-2006119504 | A2 | 11/2006 |
| WO | WO-2007147478 | A1 | 12/2007 |
| WO | WO-2008136756 | A1 | 11/2008 |
| WO | WO-2010033168 | A2 | 3/2010 |
| WO | WO-2011062550 | A1 | 5/2011 |
| WO | WO-2014117274 | A1 | 8/2014 |
| WO | WO-2016091776 | A1 | 6/2016 |
| WO | WO-2017160569 | A1 | 9/2017 |
| WO | WO-2018064135 | A1 | 4/2018 |
| WO | WO-2019064079 | A2 | 4/2019 |
| WO | WO-2020099923 | A1 | 5/2020 |
| WO | WO-2020112890 | A1 | 6/2020 |
| WO | WO-2020135771 | A1 | 7/2020 |
| WO | WO-2020174283 | A1 | 9/2020 |
| WO | WO-2021161105 | A1 | 8/2021 |
| WO | WO-2021161109 | A1 | 8/2021 |

OTHER PUBLICATIONS

Gardner et al. (Computers and Chemical Engineering 28 (2004) 943-953) (Year: 2004).*
Abdulqawi et al. P2X3 receptor antagonist (AF-219) in refractory chronic cough: a randomised, double-blind, placebo-controlled phase 2 study. Lance 385(9974):1198-1205 (2015).
Baviskar et al.: N-fused imidazoles as novel anticancer agents that inhibit catalytic activity of topoisomerase llα and induce apoptosis in G1/S phase. J Med Chem. 54(14):5013-5030 (2011).
Berge et al.: Pharmaceutical Salts. Journal of Pharmaceutical Science. 66:1-19 (1997).
Bernstein: Crystal Structure Prediction and Polymorphism. ACA Transactions. 39:14-23 (2004).
Braga et al.: Making crystals from crystals: a green route to crystal engineering and polymorphism. Chem. Commun. 3635-3645 (2005).
Byrn et al.: Pharmaceutical Solids: A Strategic Approach to Regulatory Considerations. Pharmaceutical Research. vol. 12, No. 7, 945-954 (1995).
Cantin et al., "Discovery of P2X3 Selective Antagonists for the Treatment of Chronic Pain." Bioorganic & Medicinal Chemistry Letters, 22(7):2565-2571, 2012.
Chauret et al., BLU-5937, A potent and selective P2X3 antagonist, for the treatment of chronic itch: evidence from pre-clinical studies. Journal of Investigative Dermatology 139(9S):S232 (2019).
Chen et al. "A P2X purinoceptor expressed by a subset of sensory neurons", Nature, 377(6548):428-431, 1995.
Chernyak and Gevorgyan, "General and Efficient Copper-Catalyzed Three-Component Coupling Reaction towards Imidazoheterocycles. One-Pot Synthesis of Alpidem and Zolpidem," Angewandte Chemie International Edition, 49(15):2743-2746, 2010.
Cockayne et al. "Urinary bladder hyporeflexia and reduced pain-related behaviour in P2X 3-deficient mice." Nature, 407(6807):1011-1015, 2000.
Deady, Ring nitrogen oxidation of amino substituted nitrogen heterocycles with m-Chloroperbenzoic acid. Syn. Comm., 7(8):509-514, 1977.
Ding et al.: P2X3 receptor involvement in endometriosis pain via ERK signaling pathway; PLOS One 12(9) pp. 1-17 (2017).
Fabbretti, ATP-gated P2X3 receptors are specialised sensors of the extracellular environment. Advances in Experimental Medicine and Biology 1051:7-16 (2017).
Ford et al., The therapeutic promise of ATP antagonism at P2X3 receptors in respiratory and urological disorders. Frontiers in Cellular Neuroscience 7:267 [1-10] (2013).
Ford, In pursuit of P2X3 antagonists: novel therapeutics for chronic pain and afferent sensitization. Purinergic Signalling 8(Suppl 1):3-26 (2012).
Garceau et al., BLU-5937: A selective P2X3 antagonist with potent anti-tussive effect and no taste alteration. Pulmonary Pharmacology and Therapeutics 56:56-62 (2019).
Garcia-Guzman et al., "Molecular characterization and pharmacological properties of the human P2X3 purinoceptor", Mol. Brain Res., 47(1-2):59-66, 1997.
Han, et al., A subpopulation of nociceptors specifically linked to itch. Nat Neurosci. Feb. 2013; 16(2):174-82. doi: 10.1038/nn.3289. Epub Dec. 23, 2012.
Jarvis et al.: A-317491, a novel potent and selective non-nucleotide antagonist of P2X3 and P2X2/3 receptors, reduces chronic inflammatory and neuropathic pain in the rat. PNAS. 99(26:17179-17184 (2002).
Jones et al.: Pharmaceutical Cocrystals: An Emerging Approach to Physical Property Enhancement. MRS Bulletin. 31:875-879 (2006).
Joule et al., Heterocyclic Chemistry, Third edition, Chapter 11, "The diazines: pyridazine, pyrimidine and pyrazine: reactions and synthesis." London: Cheapman and Hall, p. 189-225, 1995.
Kamei et al., Involvement of ionotropic purinergic receptors in the histamine-induced enhancement of the cough reflex sensitivity in guinea pigs. Eur J Pharmacol 547:160-164, 2006.
Kamei et al., Involvement of P2X receptor subtypes in ATP-induced enhancement of the cough reflex sensitivity. Eur J Pharmacol 528:158-161, 2005.
Kwong et al., P2X2 receptors differentiate placodal vs. neural crest C-fiber phenotypes innervating guinea pig lungs and esophagus. AJP Lung Cell Mol Physiol., 295:L858-L865, 2008.
Lewis et al. "Coexpression of P2X2 and P2X3 receptor subunits can account for ATP-gated currents in sensory neurons", Nature, 377(6548):432-435, 1995.
Lombardo et al., Discovery of N-(2-Chloro-6-methyl-phenyl)-2-(6-(4-(2-hydroxyethyl)-piperazin-1-yl)-2-methylpyrimidin-4-ylamino)thiazole-5-carboxamide (BMS-354825), a Dual Src/Abl kinase inhibitor with potent antitumor activity in preclinical assays. J. Med. Chem., 47: 6658-6661, 2004.
Mackenzie et al., Drug Discovery Today: Disease Models, 1(3):297-302, 2004.
Marucci et al., Update on novel purinergic P2X3 and P2X2/3 receptor antagonists and their potential therapeutic applications. Expert Opinion on Therapeutic Patents 29(12):943-963 (2019).
North, The P2X3 subunit: a molecular target in pain therapeutics. Current Opinion in Investigational Drugs 4(7):833-840 (2003).
PCT/CA2014/050062 International Preliminary Report on Patentability dated Aug. 4, 2015.
PCT/CA2014/050062 International Search Report and Written Opinion dated Apr. 29, 2014.
PCT/IB2018/001513 International Preliminary Report on Patentability dated Apr. 2, 2020.
PCT/IB2018/001513 International Search Report and Written Opinion dated Apr. 2, 2019.
PCT/IB2019/001122 International Preliminary Report on Patentability dated Apr. 22, 2021.
PCT/IB2019/001122 International Search Report and Written Opinion dated Feb. 10, 2020.
PCT/IB2019/001199 International Preliminary Report on Patentability dated May 27, 2021.
PCT/IB2019/001199 International Search Report and Written Opinion dated Mar. 3, 2020.

(56) References Cited

OTHER PUBLICATIONS

PCT/IB2020/000160 International Preliminary Report on Patentability dated Sep. 2, 2021.
PCT/IB2020/000160 International Search Report and Written Opinion dated Jun. 15, 2020.
PCT/IB2021/000091 International Search Report and Written Opinion dated May 25, 2021.
PCT/IB2021/000130 International Search Report and Written Opinion dated Jun. 14, 2021.
Price: The computational prediction of pharmaceutical crystal structures and polymorphism. Advanced Drug Delivery Reviews. 56:301-319 (2004).
Shiratori-Hayashi et al., Role of P2X3 receptors in scratching behavior in mouse models. Journal of Allergy and Clinical Immunology 143(3):1252-1254 (2019).
Silverman et al. Chapter 8: Prodrugs and drug delivery systems. In: The Organic Chemistry of Drug Design and Drug Action. San Diego: Academic Press, Inc. p. 352-401 (1992).
Trower et al., Neurokinin-1 receptor antagonist orvepitant is an effective inhibitor of itch-associated response in a Mongolian gerbil model of scratching behaviour. Experimental Dermatology 23(11):858-860 (2014).
Ugo Basile 2012 Catalog; https://analab.gr/wp-content/uploads/Ugo-Basile-Catalogue-2012.pdf XP055483468 (2012).
U.S. Appl. No. 16/375,773 Office Action dated Jul. 9, 2019.
Vilotti et al.: B-Type Natriuretic Peptide-Induced Delayed Modulation of TRPV1 and P2X3 Receptors of Mouse Trigeminal Sensory Neurons. PLoS One. 8(11):e81138 (2013).
Yuan et al.: Effect of A-3177491 delivered by glycolipid-like polymer micelles on endometriosis pain. Int. J. Nanomedicine. 12:8171-8183 (2017).
Zhong et al., Bladder and cutaneous sensory neurons of the rat express different functional P2X receptors. Neuroscience, 120(3):667-675, 2003.
Balbach, S., et al., “Pharmaceutical evaluation of early development candidates The 100 mg approach”, International Journal of Pharmaceutics, 2004, vol. 275, p. 1-12.
Braga et al., “Crystal Polymorphism and Multiple Crystal Forms”, 2009, pp. 25-50.
Caira M R, “Crystalline Polymorphism of Organic Compounds”, Topics in Current Chemistry, Springer, Berlin, DE, (Jan. 1, 1998), vol. 198, ISSN 0340-1022, pp. 163-208.
Hilfker, Rolf, “Relevance of Solid-State Properties for Pharmaceutical Products”, 2006, pp. 1-19.
Hirayama, “Handbook for organic compounds crystal preparation”, 2008, pp. 17-23, 37-40, 45-51, 57-65 (document to present well-known arts). Machine translation attached.
Singhal, D. et al., “Drug polymorphism and dosage form design: a practical perspective”, Advanced Drug Delivery Reviews, 2004, vol. 56, p. 335-347.
Polymorphism in pharmaceutical solids; edited by Brittain HG, Marcel Dekker Inc., Grant DJW (chapter 1) pp. 1-55, Guillory JK (chapter 5) pp. 183-226, ISBN: 0-8247-0237-9, Dec. 31, 1999.
Yang L., et al., “Drug Crystalline Forms,” People’s Medical Publishing House, 2009, vol. 2, pp. 1-12, 28 Pages.

* cited by examiner (1) Heating Type A1 to 115 °C and cooling to 30 °C with $N_2$ purging

CRYSTALLINE FORMS OF A SUBSTITUTED IMIDAZOPYRIDINE COMPOUND AND USE THEREOF AS P2X3 MODULATOR

CROSS-REFERENCE

This application claims benefit of U.S. Provisional Application No. 62/760,307, filed on Nov. 13, 2018, which is herein incorporated by reference in its entirety.

BACKGROUND

P2X purinoreceptors are a family of ion channels that are activated by extracellular adenosine triphosphate (ATP). Purinoreceptors have been implicated in a variety of biological functions, especially those related to pain sensitivity. The P2X3 receptor subunit is a member of this family.

P2X3 is selectively expressed on nociceptive, small diameter sensory neurons (i.e., neurons that are stimulated by pain or injury), which is consistent with a role in pain sensitivity. Blocking P2X3 receptors has been reported to be analgesic in animal models of chronic inflammatory and neuropathic pain. Jarvis, et al., PNAS, 99, 17179-17184 (2002). It is, therefore, believed that reducing the P2X3 level or activity would be useful for modulating pain sensation in a subject suffering from pain and other disorders associated with P2X3 activity.

SUMMARY OF THE INVENTION

Described herein is the P2X3 modulator methyl (S)-2-((2-(2,6-difluoro-4-(methylcarbamoyl)phenyl)-7-methylimidazo[1,2-a]pyridin-3-yl)methyl)morpholine-4-carboxylate, including pharmaceutically acceptable solvates (including hydrates), polymorphs, and amorphous phases, and methods of uses thereof. In some embodiments, methyl (S)-2-((2-(2,6-difluoro-4-(methylcarbamoyl)phenyl)-7-methylimidazo[1,2-a]pyridin-3-yl)methyl)morpholine-4-carboxylate is used in the manufacture of medicaments for the treatment of diseases or conditions that are associated with P2X3 activity.

Also described herein are methods for preparing crystalline forms of methyl-2-((2-(2,6-difluoro-4-(methylcarbamoyl)phenyl)-7-methylimidazo[1,2-a]pyridin-3-yl)methyl)morpholine-4-carboxylate. Further described are pharmaceutical compositions that include the crystalline forms of methyl (S)-2-((2-(2,6-difluoro-4-(methylcarbamoyl)phenyl)-7-methylimidazo[1,2-a]pyridin-3-yl)methyl)morpholine-4-carboxylate and methods of using the compound in the treatment of diseases or conditions.

In one aspect, described herein is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, or a solvate thereof.

In some embodiments, the crystalline form of methyl (S)-2-((2-(2,6-difluoro-4-(methylcarbamoyl)phenyl)-7-methylimidazo[1,2-a]pyridin-3-yl)methyl)morpholine-4-carboxylate comprises the Type A* family of crystalline forms selected from the group consisting of Type A0, Type A, Type A1, Type A2, and Type A3, having at least one of the following properties:

(a) an X-ray powder diffraction (XRPD) pattern substantially the same as shown in FIG. 1;

(b) an X-ray powder diffraction (XRPD) pattern with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta;

(c) a thermo-gravimetric analysis (TGA) substantially similar to the one set forth in FIG. 2;

(d) a DSC thermogram substantially similar to the one set forth in FIG. 2;

(e) a DSC thermogram with an endotherm having an onset at about 167° C.; or (f) combinations thereof.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form has an X-ray powder diffraction (XRPD) pattern substantially the same as shown in FIG. 1.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form has an X-ray powder diffraction (XRPD) pattern with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form has a thermo-gravimetric analysis (TGA) substantially similar to the one set forth in FIG. 2.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form has a DSC thermogram substantially similar to the one set forth in FIG. 2.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form has a DSC thermogram with an endotherm having an onset at about 167° C.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is characterized as having properties: (a) an X-ray powder diffraction (XRPD) pattern substantially the same as shown in FIG. 1; (b) an X-ray powder diffraction (XRPD) pattern with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta; (c) a thermo-gravimetric analysis (TGA) substantially similar to the one set forth in FIG. 2; (d) a DSC thermogram substantially similar to the one set forth in FIG. 2; and (e) a DSC thermogram with an endotherm having an onset at about 167° C.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is obtained from acetonitrile, acetone, tert-butyl methyl ether, water, methanol, ethanol, isopropanol, propanol, butanol, diethyleneglycol, ethyl acetate, isopropyl acetate, tetrahydrofuran, 2-methyltetrahydrofuran, dimethylsulfoxide, dimethylformamide, methyl ethyl ketone, methyl isobutyl ketone, butyl acetate, hexane, heptane, dichloromethane, chloroform, 1,2-dichloroethane, dimethoxyethane, toluene, anisole, or combinations thereof.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form comprises the Type A* family of crystalline forms selected from the group consisting of Type A0, Type A, and Type A1.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is Type A0.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is Type A.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is Type A1.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is Type A2.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is Type A3.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate for use in medicine.

In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is a hydrate. In some embodiments is a crystalline form of methyl (S)-2-((2-(2,6-difluoro-4-(methylcarbamoyl)phenyl)-7-methylimidazo[1,2-a]pyridin-3-yl)methyl)morpholine-4-carboxylate, wherein the crystalline form is a channel hydrate.

In another aspect, described herein is a pharmaceutical composition comprising a crystalline form of methyl (S)-2-((2-(2,6-difluoro-4-(methylcarbamoyl)phenyl)-7-methylimidazo[1,2-a]pyridin-3-yl)methyl)morpholine-4-carboxylate and at least one inactive ingredient selected from pharmaceutically acceptable carriers, diluents, and excipients. In some embodiments, the methyl (S)-2-((2-(2,6-difluoro-4-(methylcarbamoyl)phenyl)-7-methylimidazo[1,2-a]pyridin-3-yl)methyl)morpholine-4-carboxylate pharmaceutical composition is formulated for administration to a mammal by intravenous administration, subcutaneous administration, oral administration, inhalation, nasal administration, topical administration, or ophthalmic administration. In some embodiments, the methyl (S)-2-((2-(2,6-difluoro-4-(methylcarbamoyl)phenyl)-7-methylimidazo[1,2-a]pyridin-3-yl)methyl)morpholine-4-carboxylate pharmaceutical composition is in the form of a tablet, a pill, a capsule, a liquid, a suspension, a gel, a dispersion, a solution, an emulsion, an ointment, or a lotion.

In another aspect, described herein is a method for treating a disorder associated with P2X3 activity, for treating pain, or for treating a urinary tract disorder in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating pain in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating a urinary tract disorder in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating a urinary tract disorder in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the urinary tract disorder comprises an overactive bladder. In some embodiments is a method for treating a urinary tract disorder in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the urinary tract disorder comprises neurogenic overactive bladder, non-neurogenic overactive bladder, interstitial cystitis, prostatitis, prostadynia, and benign prostatic hyperplasia.

In another aspect, described herein is a method of reducing or preventing uncontrolled loss of urine in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method of reducing or preventing uncontrolled loss of urine in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the uncontrolled loss of urine is associated with urge incontinence, cough incontinence, stress incontinence, overflow incontinence, functional incontinence, neurogenic incontinence, post-prostatectomy incontinence, urinary urgency, nocturia, and enuresis.

In another aspect, described herein is a method for treating cough in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating cough in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the cough is chronic cough. In some embodiments is a method for treating cough in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the cough is associated with a disease, disorder, or condition selected from chronic obstructive pulmonary disease, asthma, tuberculosis, bronchitis, bronchiectasis, suppurative pulmonary disease, respiratory malignancies, allergy, cystic fibrosis, pulmonary fibrosis, respiratory tract inflammation, emphysema, pneumonia, lung cancer, lung neoplasia, sore throat, common cold, influenza, respiratory tract infection, bronchoconstriction, sarcoidosis, viral or bacterial infection of the upper airways, angiotension converting enzyme (ACE) inhibitor therapy, smoker's cough, chronic non-productive cough, neoplastic cough, cough due to gastroesophageal reflux, and inhalation of irritants, smoke, smog, dust, or air pollution.

In another aspect, described herein is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with an inflammatory skin disease, an infectious skin disease, an autoimmune skin disease, or a pregnancy-related skin disease. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with an inflammatory skin disease selected from the group consisting of atopic dermatitis, allergic, irritant contact dermatitis, exsiccation dermatitis, nummular and dyshidrotic dermatitis, lichen planus, lichen sclerosus et atrophicus, polymorphous light eruption psoriasis, Grover's disease, mucinosis, mastocytosis, and urticaria. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with an infectious skin disease selected from the group consisting of mycoses, bacterial and viral infections, scabies, pediculosis, insect bites, and folliculitides. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with an autoimmune skin disease selected from the group consisting of dermatitis herpetiformis (Duhring's disease), bullous pemphigoid; genodermatoses, Darier's disease, and Hailey-Hailey disease. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with a pregnancy-related skin disease selected from the group consisting of polymorphic eruption of pregnancy (PEP), atopic eruption of pregnancy, pemphigoid gestationis, neoplasias, and cutaneous T-cell lymphoma. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with prurigo nodularis. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with a kidney disease or a therapeutic procedure to treat a kidney disease. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with a chronic kidney disease. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with a therapeutic procedure to treat a kidney disease, wherein the therapeutic procedure to treat the kidney disease is selected from the group consisting of hemodialysis and peritoneal dialysis. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with a medical procedure or treatment. In some embodiments is a method for treating pruritus in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the pruritus is associated with a medical treatment with a drug selected from the group consisting of opioids, anti-malarial drugs, anti-cancer therapies and epidermal growth factor receptor inhibitors.

In another aspect, described herein is a method for treating endometriosis, endometriosis-associated pain, and endometriosis-associated symptoms in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating endometriosis in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating endometriosis-associated pain in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4- carboxylate described herein. In some embodiments is a method for treating endometriosis-associated symptoms in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein. In some embodiments is a method for treating endometriosis-associated symptoms in a mammal in need thereof, comprising administering to the mammal in need thereof a therapeutically effective amount of a crystalline form of methyl (S)-2-((2-(2,6-difluoro-4-(methylcarbamoyl)phenyl)-7-methylimidazo[1,2-a]pyridin-3-yl)methyl)morpholine-4-carboxylate described herein, wherein the endometriosis-associated symptoms are selected from dysmenorrhea, dyspareunia, dysuria, and dyschezia.

In some embodiments of the methods described herein, the mammal is a human.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described.

INCORPORATION BY REFERENCE

All publications, patents, and patent applications mentioned in this specification are herein incorporated by reference to the extent applicable and relevant and to the same extent as if each individual publication, patent, or patent application was specifically and individually indicated to be incorporated by reference.

DETAILED DESCRIPTION OF THE INVENTION

Figure 1:
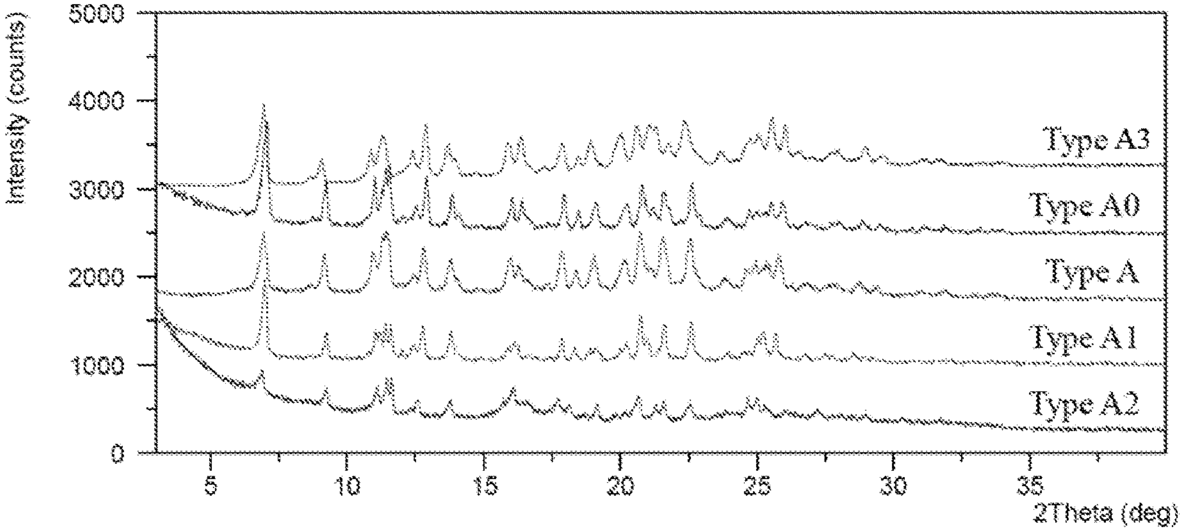
FIG. 1. Illustrates an XRPD spectrum of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family (Type A, Type A0, Type A1, Type A02, and Type A3).

Described herein are crystalline forms of P2X3 modulator methyl-2-((2-(2,6-difluoro-4-(methylcarbamoyl)phenyl)-7-methylimidazo[1,2-a]pyridin-3-yl)methyl)morpholine-4-carboxylate. Also described herein are pharmaceutical compositions that include the crystalline forms of methyl (S)-2-((2-(2,6-difluoro-4-(methylcarbamoyl)phenyl)-7-methylimidazo[1,2-a]pyridin-3-yl)methyl)morpholine-4-carboxylate and methods of using the compound in the treatment of diseases or conditions.

Compound 1

As described herein, Compound 1 is methyl (S)-2-((2-(2,6-difluoro-4-(methylcarbamoyl)phenyl)-7-methylimidazo[1,2-a]pyridin-3-yl)methyl)morpholine-4-carboxylate. "Compound 1" or "methyl (S)-2-((2-(2,6-difluoro-4-(methylcarbamoyl)phenyl)-7-methylimidazo[1,2-a]pyridin-3-yl)methyl)morpholine-4-carboxylate" refers to the compound with the following structure:

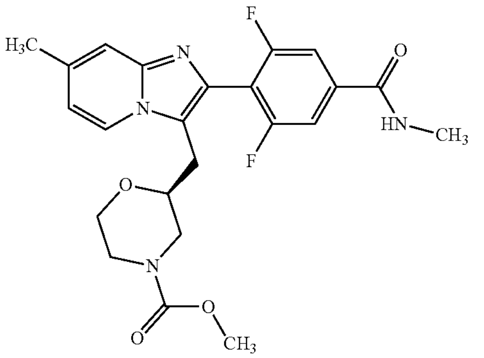

In some embodiments, Compound 1 includes the solvent addition forms (solvates). Solvates contain either stoichiometric or non-stoichiometric amounts of a solvent, and are formed during the process of product formation or isolation with pharmaceutically acceptable solvents such as water, ethanol, methanol, tert-butyl methyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In some embodiments, solvates are formed using, but not limited to, Class 3 solvent(s). In some embodiments, solvates are formed using, but not limited to, Class 2 solvent(s). Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016). Hydrates are formed when the solvent is water, or alcoholates are formed when the solvent is alcohol.

In other embodiments, Compound 1 is prepared in various forms, including but not limited to, an amorphous phase, crystalline forms, milled forms, and nano-particulate forms.

While not intending to be bound by any particular theory, certain solid forms are characterized by physical properties, e.g., stability, solubility, and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein.

Crystalline Forms

The identification and selection of a solid form of a pharmaceutical compound are complex, given that a change in solid form may affect a variety of physical and chemical properties, which may provide benefits or drawbacks in processing, formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable, and marketable pharmaceutical product.

Crystalline Compound 1, Type A* Family (Type A, Type A0, Type A1, Type A2, and Type A3)

Figure 3:
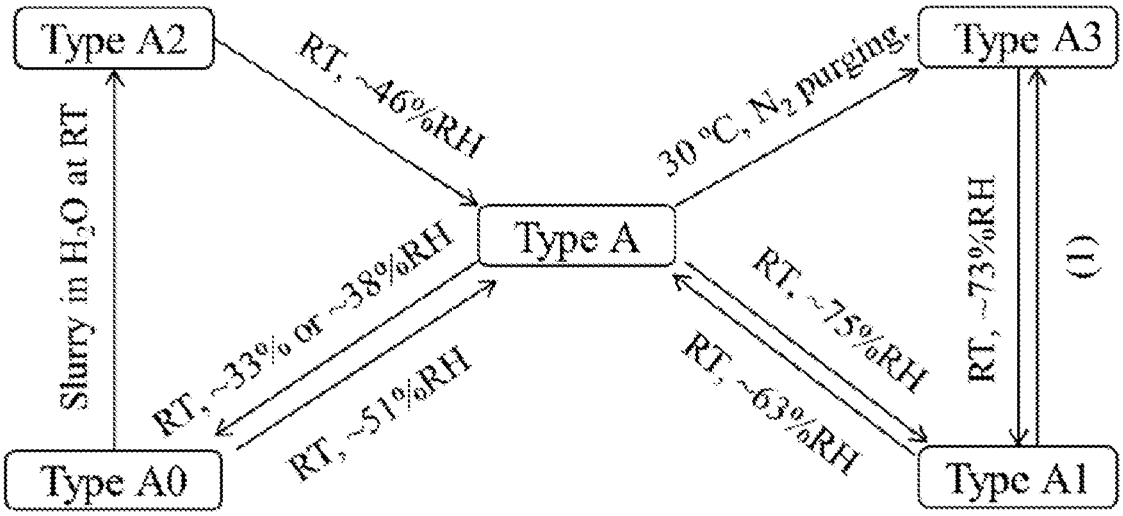
FIG. 3. Illustrates the conversion relationship of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family.

A series of Compound 1 crystal forms (Type A, Type A0, Type A1, Type A2, and Type A3) were found which show similar diffraction patterns (FIG. 1). These crystal forms convert to each other under different humidity conditions (Table 1 and FIG. 3).

TABLE 1

| Crystal form | Conversion conditions | Relative humidity |
|---|---|---|
| Type A3 | $N_2$ purging of Type A at 30° C. | $N_2$ purging |
| Type A3 | Heating Type A1 to 115° C. and then cooling to 30° C. with $N_2$ purging | $N_2$ purging |
| Type A0 | Storage of Type A1 under ambient conditions | ~33% or ~38%RH |
| Type A | Storage of Type A2 under ambient conditions | ~46%RH |
| Type A | Storage of Type A0 under ambient conditions | ~51%RH |
| Type A | Storage of Type A1 under ambient conditions | ~63%RH |
| Type A1 | Storage of Type A3 under ambient conditions | ~73%RH |
| Type A1 | Storage of Type A under ambient conditions | ~75%RH |
| Type A2 | Slurry of Type A0 in $H_2O$ at RT | $H_2O$ |

Therefore, the crystal five forms (Type A, Type A0, Type A1, Type A2, and Type A3) are attributed to the same crystal family (Type A* family). The interconversion among Type A* family crystal forms is caused by different amounts of water residing in the crystal lattice resulting in slight peak shifts in the XRPD patterns.

Figure 2:
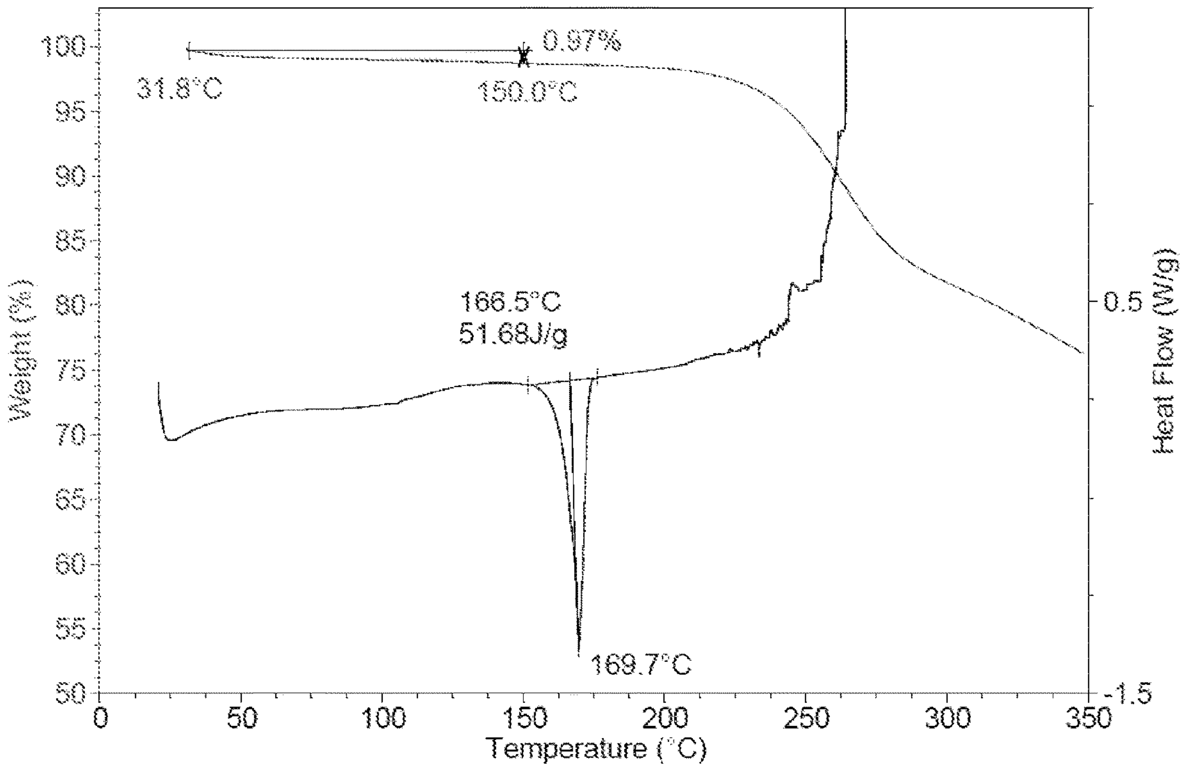
FIG. 2. Illustrates a TGA and DSC thermogram of crystalline (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family crystalline form (Type A0).

In some embodiments, Compound 1 is crystalline. In some embodiments, Compound 1 is crystalline and a hydrate. In some embodiments, Compound 1 is crystalline and a channel hydrate. In some embodiments, crystalline Compound 1 comprises the Type A* family of crystalline forms selected from the group consisting of Type A0, Type A, Type A1, Type A2, and Type A3. In some embodiments, crystalline Compound 1 comprises the Type A* family of crystalline forms selected from the group consisting of Type A0, Type A, Type A1, Type A2, and Type A3 and is characterized as having at least one of the following properties:

(a) an X-ray powder diffraction (XRPD) pattern substantially the same as shown in FIG. 1;

(b) an X-ray powder diffraction (XRPD) pattern with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta;

(c) a thermo-gravimetric analysis (TGA) substantially similar to the one set forth in FIG. 2;

(d) a DSC thermogram substantially similar to the one set forth in FIG. 2;

(e) a DSC thermogram with an endotherm having an onset at about 167° C.; or (f) combinations thereof.

In some embodiments, crystalline Compound 1, Type A* Family, is characterized as having at least two of the properties selected from (a) to (e). In some embodiments, crystalline Compound 1, Type A* Family, is characterized as having at least three of the properties selected from (a) to (e). In some embodiments, crystalline Compound 1, Type A* Family, is characterized as having at least four of the properties selected from (a) to (e). In some embodiments, crystalline Compound 1, Type A* Family, is characterized as having properties (a) to (e).

In some embodiments, crystalline Compound 1, Type A* Family, has an X-ray powder diffraction (XRPD) pattern substantially the same as shown in FIG. 1. In some embodiments, crystalline Compound 1, Type A* Family, has an X-ray powder diffraction (XRPD) pattern with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta. In some embodiments, crystalline Compound 1, Type A* Family, has a thermo-gravimetric analysis (TGA) thermogram substantially similar to the one set forth in FIG. 2. In some embodiments, crystalline Compound 1, Type A* Family, has a DSC thermogram substantially similar to the one set forth in FIG. 2. In some embodiments, crystalline Compound 1, Type A* Family, has a DSC thermogram with an endotherm having an onset at about 167° C.

In some embodiments, crystalline Compound 1 comprises the Type A* family of crystalline forms selected from the group consisting of Type A0, Type A, and Type A1. In some embodiments, the Compound 1 crystalline form is Type A0. In some embodiments, the Compound 1 crystalline form is Type A. In some embodiments, the Compound 1 crystalline form is Type A1. In some embodiments, the Compound 1 crystalline form is Type A2. In some embodiments, the Compound 1 crystalline form is Type A3.

Crystalline Compound 1, Type K

Figure 12:
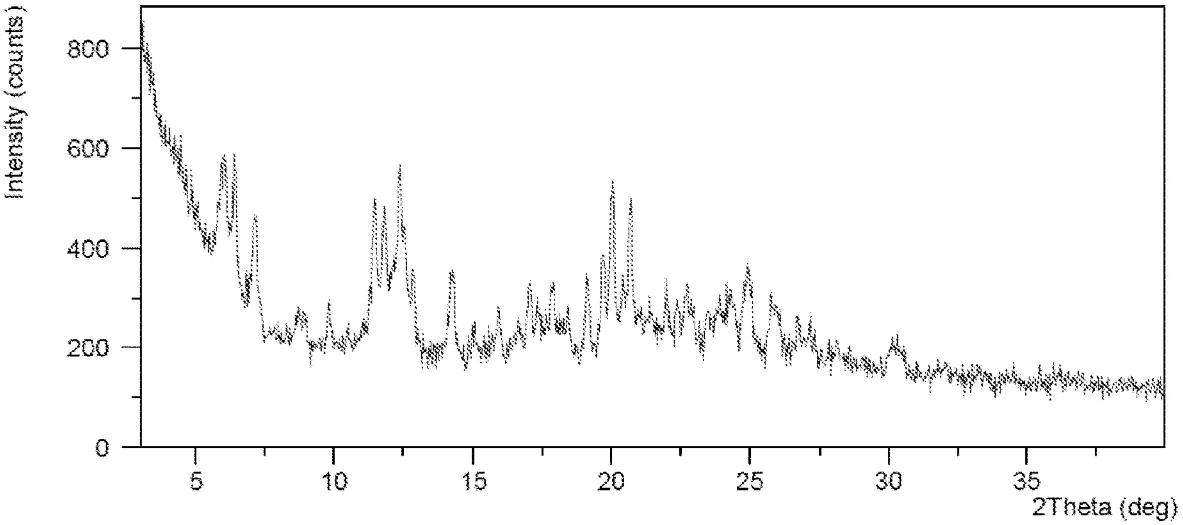
FIG. 12. Illustrates an XRPD spectrum of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type K.
Figure 13:
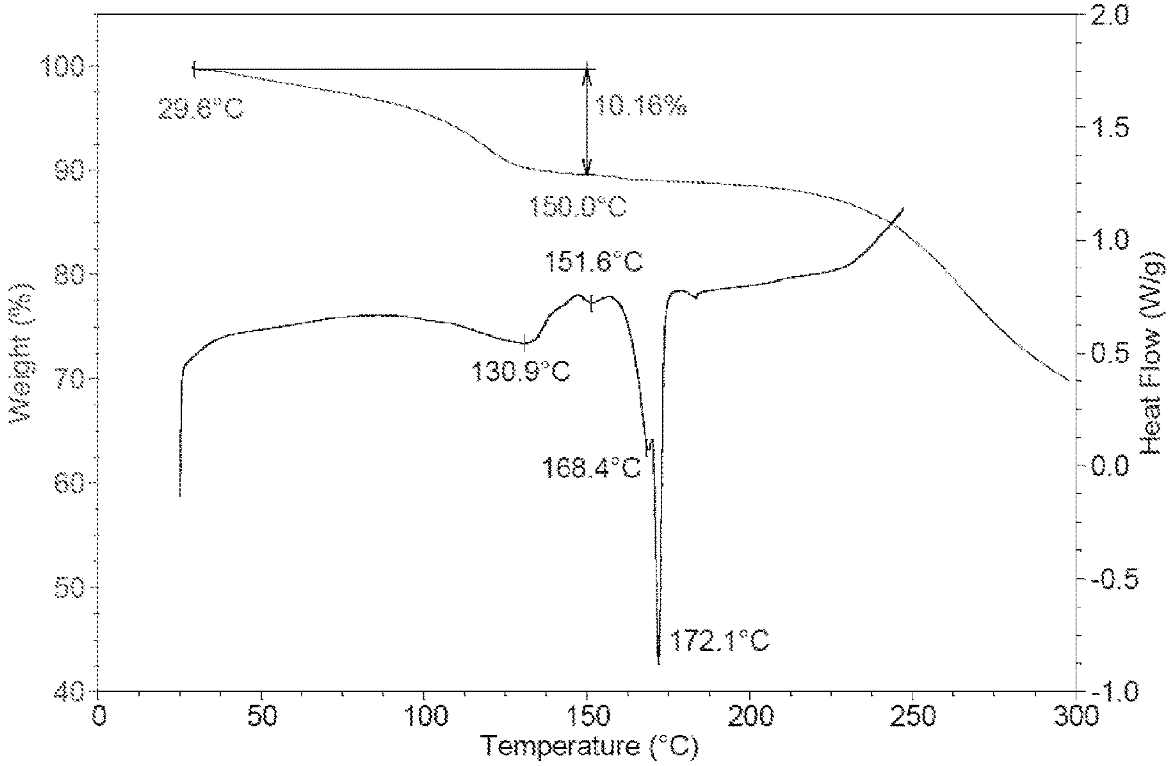
FIG. 13. Illustrates a TGA and DSC thermogram of crystalline (S)-2-((2-(2,6-difluoro-4-(methylcarbamoyl)phenyl)-7-methylimidazo[1,2-a]pyridin-3-yl)methyl)morpholine-4-carboxylate (Compound 1), Type K.

In some embodiments, the crystalline form of Compound 1 is crystalline Type K. Crystalline Type K of Compound 1 is characterized as having at least one of the following properties:

(a) an X-ray powder diffraction (XRPD) pattern substantially the same as shown in FIG. 12;

(b) an X-ray powder diffraction (XRPD) pattern with characteristic peaks at about 11.4° 2-Theta, 11.8° 2-Theta, 12.3° 2-Theta, 20.0° 2-Theta, and 20.7° 2-Theta;

(c) a thermo-gravimetric analysis (TGA) substantially similar to the one set forth in FIG. 13;

(d) a DSC thermogram substantially similar to the one set forth in FIG. 13;

(e) a DSC thermogram with multiple endotherms at about 131° C., 152° C., 168° C., and 172° C.; or (f) combinations thereof.

In some embodiments, crystalline Compound 1, Type K, is characterized as having at least two of the properties selected from (a) to (e). In some embodiments, crystalline Compound 1, Type K, is characterized as having at least three of the properties selected from (a) to (e). In some embodiments, crystalline Compound 1, Type K, is characterized as having at least four of the properties selected from (a) to (e). In some embodiments, crystalline Compound 1, Type K, is characterized as having properties (a) to (e).

In some embodiments, crystalline Compound 1, Type K, has an X-ray powder diffraction (XRPD) pattern substantially the same as shown in FIG. 12. In some embodiments, crystalline Compound 1, Type K, has an X-ray powder diffraction (XRPD) pattern with characteristic peaks at about 11.4° 2-Theta, 11.8° 2-Theta, 12.3° 2-Theta, 20.0° 2-Theta, and 20.7° 2-Theta. In some embodiments, crystalline Compound 1, Type K, has a thermo-gravimetric analysis (TGA) thermogram substantially similar to the one set forth in FIG. 13.

In some embodiments, crystalline Compound 1, Type K, has a DSC thermogram substantially similar to the one set forth in FIG. 13. In some embodiments, crystalline Compound 1, Type K, has a DSC thermogram with multiple endotherms at about 131° C., 152° C., 168° C., and 172° C.

In some embodiments, crystalline Compound 1, Type K, is a hydrate. In some embodiments, crystalline Compound 1, Type K, is a solvate. In some embodiments, crystalline Compound 1, Type K, is solvated with isopropyl acetate. In some embodiments crystalline Compound 1, Type K, is unsolvated. In some embodiments, crystalline Compound 1, Type K, is anhydrous. Crystalline Compound 1, Type N In some embodiments, the crystalline form of Compound 1 is crystalline Type N.

Figure 14:
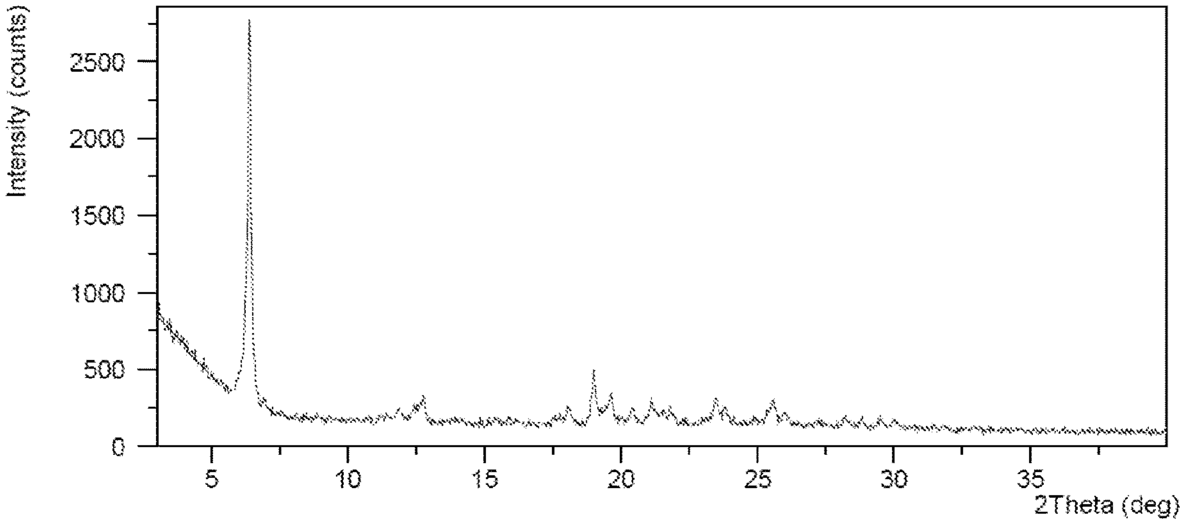
FIG. 14. Illustrates an XRPD spectrum of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type N.
Figure 15:
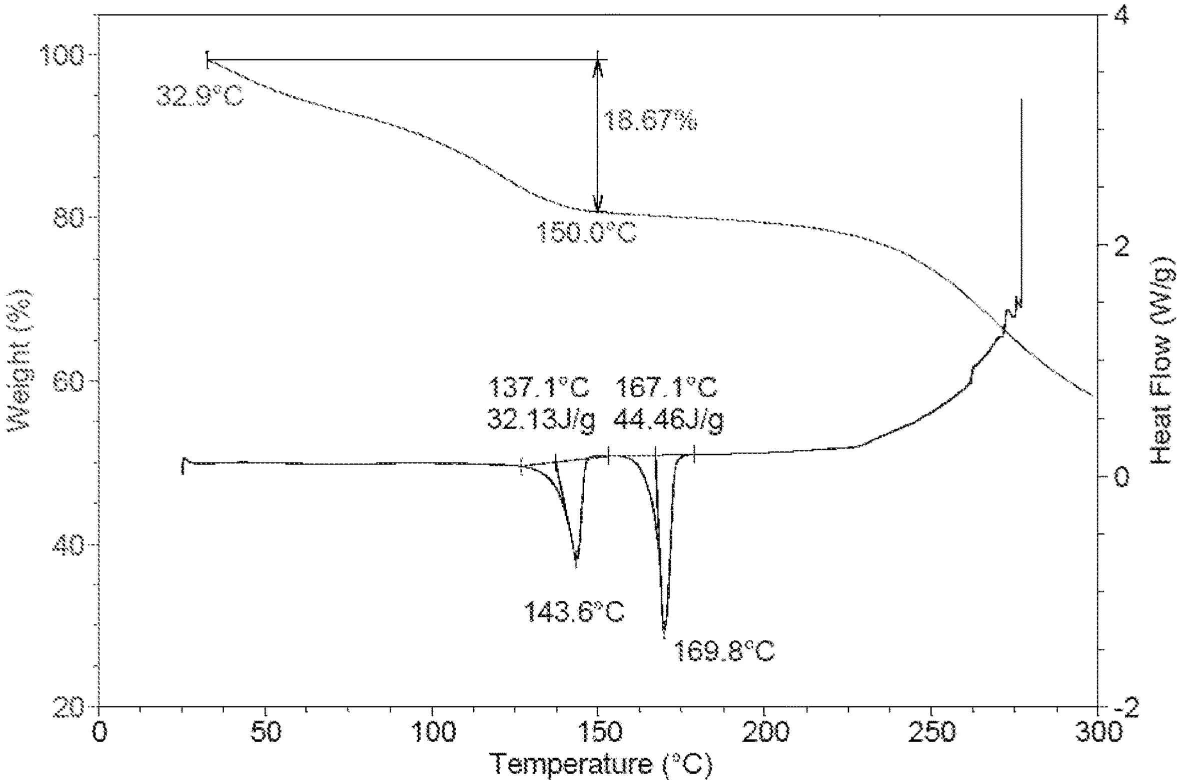
FIG. 15. Illustrates a TGA and DSC thermogram of crystalline (S)-2-((2-(2,6-difluoro-4-(methylcarbamoyl)phenyl)-7-methylimidazo[1,2-a]pyridin-3-yl)methyl)morpholine-4-carboxylate (Compound 1), Type N.

Crystalline Type N of Compound 1 is characterized as having at least one of the following properties:

(a) an X-ray powder diffraction (XRPD) pattern substantially the same as shown in FIG. 14;

(b) an X-ray powder diffraction (XRPD) pattern with characteristic peaks at about 6.4° 2-Theta, 19.0° 2-Theta, and 19.6° 2-Theta;

(c) a thermo-gravimetric analysis (TGA) substantially similar to the one set forth in FIG. 15;

(d) a DSC thermogram substantially similar to the one set forth in FIG. 15;

(e) a DSC thermogram with two endotherms at about 144° C. and 170° C.; or (f) combinations thereof.

In some embodiments, crystalline Compound 1, Type N, is characterized as having at least two of the properties selected from (a) to (e). In some embodiments, crystalline Compound 1, Type N, is characterized as having at least three of the properties selected from (a) to (e). In some embodiments, crystalline Compound 1, Type N, is characterized as having at least four of the properties selected from (a) to (e). In some embodiments, crystalline Compound 1, Type N, is characterized as having properties (a) to (e).

In some embodiments, crystalline Compound 1, Type N, has an X-ray powder diffraction (XRPD) pattern substantially the same as shown in FIG. 14. In some embodiments, crystalline Compound 1, Type N, has an X-ray powder diffraction (XRPD) pattern with characteristic peaks at about 6.4° 2-Theta, 19.0° 2-Theta, and 19.6° 2-Theta. In some embodiments, crystalline Compound 1, Type N, has a thermo-gravimetric analysis (TGA) thermogram substantially similar to the one set forth in FIG. 15. In some embodiments, crystalline Compound 1, Type N, has a DSC thermogram substantially similar to the one set forth in FIG. 15. In some embodiments, crystalline Compound 1, Type N, has a DSC thermogram with two endotherms at about 144° C. and 170° C. In some embodiments, crystalline Compound 1, Type N, is a hydrate. In some embodiments, crystalline Compound 1, Type N, is a solvate. In some embodiments, crystalline Compound 1, Type N, is solvated with butyl acetate. In some embodiments crystalline Compound 1, Type N, is unsolvated. In some embodiments, crystalline Compound 1, Type N, is anhydrous.

Crystalline Compound 1, Type O

Figure 16:
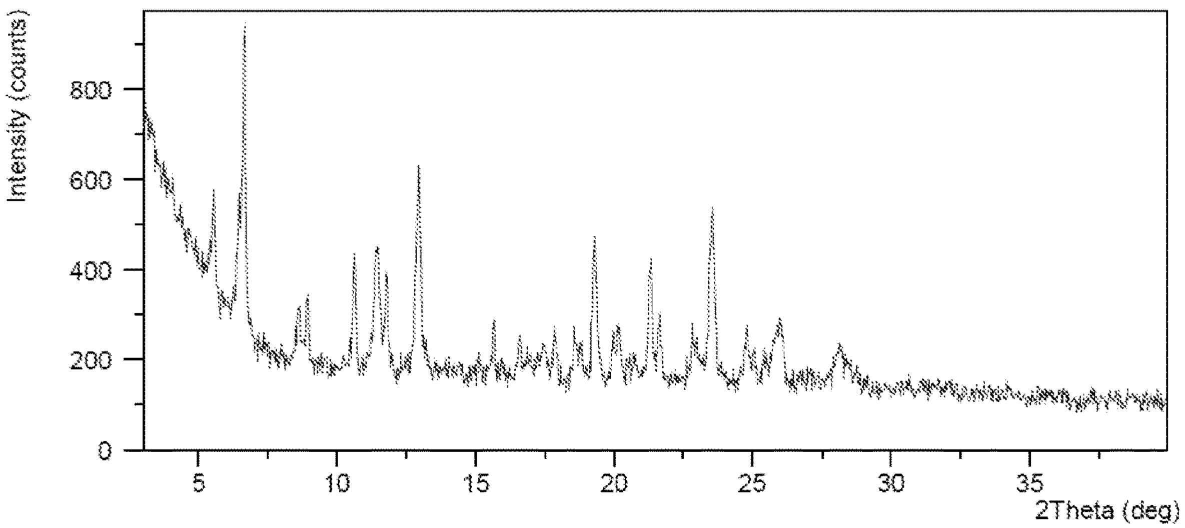
FIG. 16. Illustrates an XRPD spectrum of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type 0.
Figure 17:
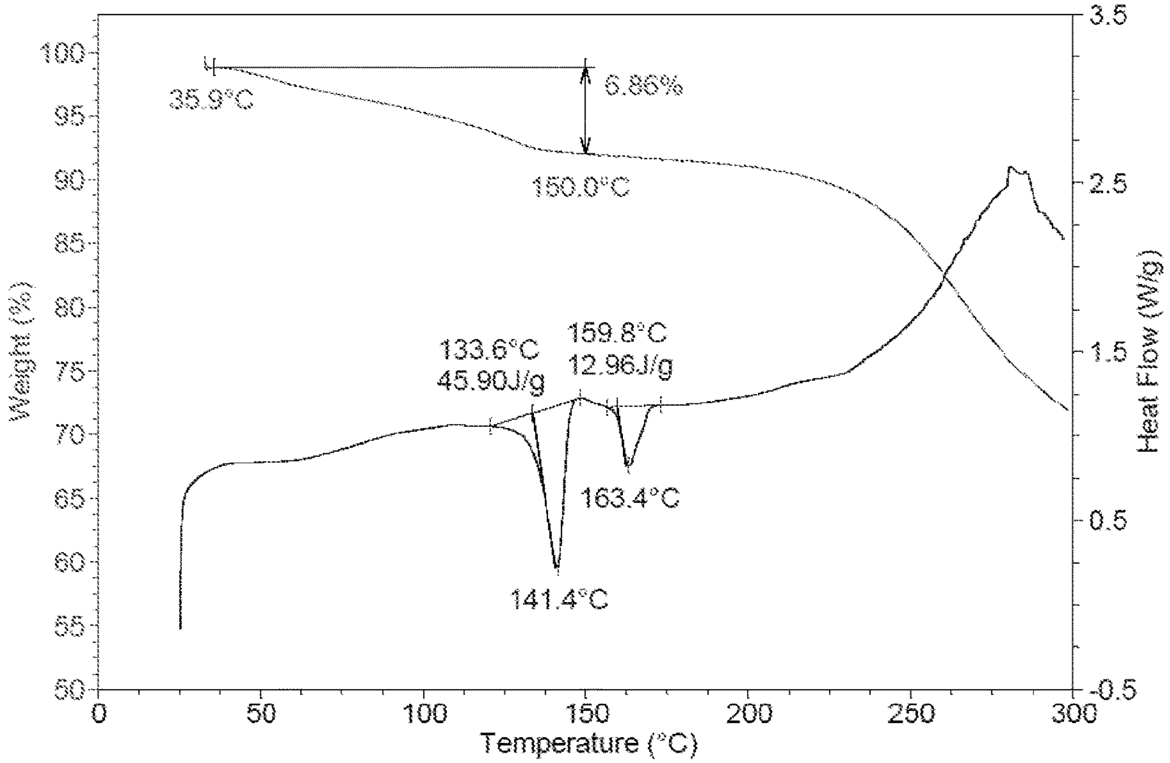
FIG. 17. Illustrates a TGA and DSC thermogram of crystalline (S)-2-((2-(2,6-difluoro-4-(methylcarbamoyl)phenyl)-7-methylimidazo[1,2-a]pyridin-3-yl)methyl)morpholine-4-carboxylate (Compound 1), Type 0.

In some embodiments, the crystalline form of Compound 1 is crystalline Type O. Crystalline Type O of Compound 1 is characterized as having at least one of the following properties:

(a) an X-ray powder diffraction (XRPD) pattern substantially the same as shown in FIG. 16;

(b) an X-ray powder diffraction (XRPD) pattern with characteristic peaks at about 6.6° 2-Theta, 12.9° 2-Theta, 19.3° 2-Theta, 21.4° 2-Theta, and 23.5° 2-Theta;

(c) a thermo-gravimetric analysis (TGA) substantially similar to the one set forth in FIG. 17;

(d) a DSC thermogram substantially similar to the one set forth in FIG. 17;

(e) a DSC thermogram with two endotherms at about 141° C. and 163° C.; or (f) combinations thereof.

In some embodiments, crystalline Compound 1, Type 0, is characterized as having at least two of the properties selected from (a) to (e). In some embodiments, crystalline Compound 1, Type O, is characterized as having at least three of the properties selected from (a) to (e). In some embodiments, crystalline Compound 1, Type O, is characterized as having at least four of the properties selected from (a) to (e). In some embodiments, crystalline Compound 1, Type O, is characterized as having properties (a) to (e).

In some embodiments, crystalline Compound 1, Type O, has an X-ray powder diffraction (XRPD) pattern substantially the same as shown in FIG. 16. In some embodiments, crystalline Compound 1, Type O, has an X-ray powder diffraction (XRPD) pattern with characteristic peaks at about 6.6° 2-Theta, 12.9° 2-Theta, 19.3° 2-Theta, 21.4° 2-Theta, and 23.5° 2-Theta. In some embodiments, crystalline Compound 1, Type O, has a thermo-gravimetric analysis (TGA) thermogram substantially similar to the one set forth in FIG. 17. In some embodiments, crystalline Compound 1, Type O, has a DSC thermogram substantially similar to the one set forth in FIG. 17. In some embodiments, crystalline Compound 1, Type O, has a DSC thermogram with two endotherms at about 141° C. and 163° C. In some embodiments, crystalline Compound 1, Type O, is a hydrate. In some embodiments, crystalline Compound 1, Type O, is a solvate. In some embodiments, crystalline Compound 1, Type O, is solvated with dimethylsulfoxide. In some embodiments crystalline Compound 1, Type O, is unsolvated. In some embodiments, crystalline Compound 1, Type O, is anhydrous.

Crystalline Compound 1, Type B

Figure 18:
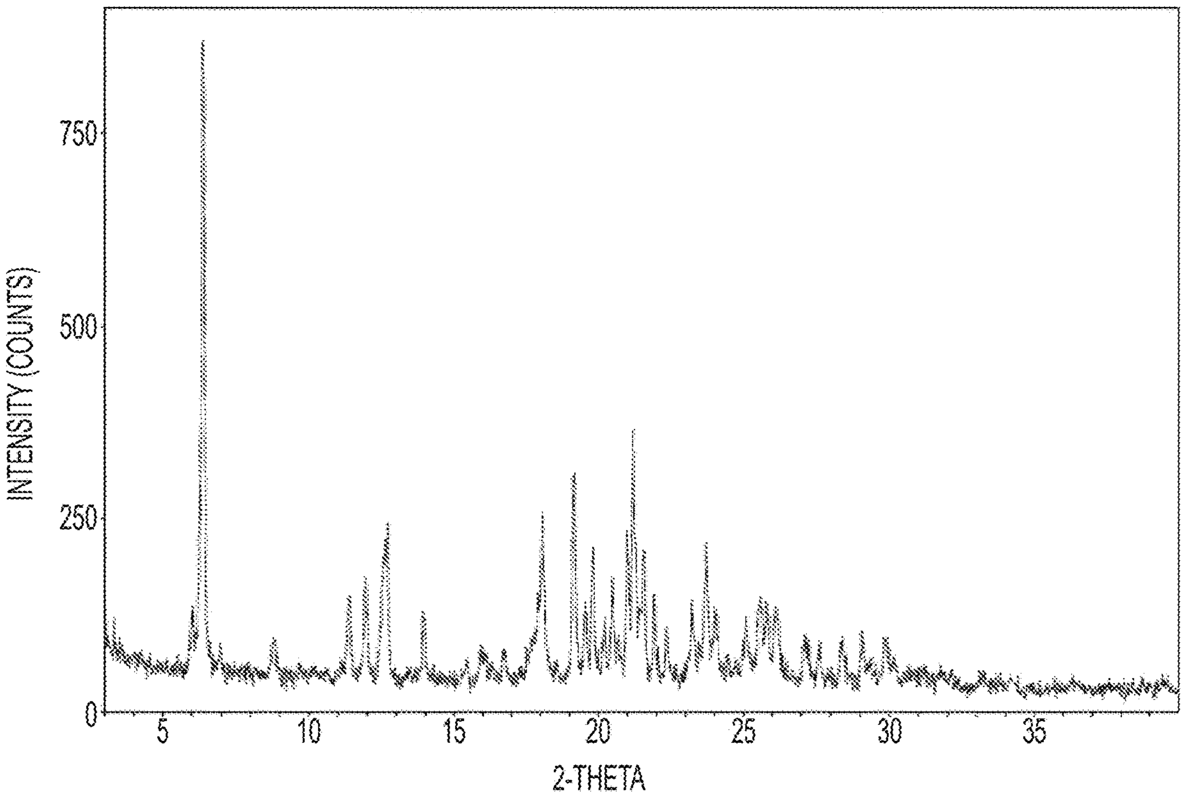
FIG. 18. Illustrates an XRPD spectrum of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type B.
Figure 19:
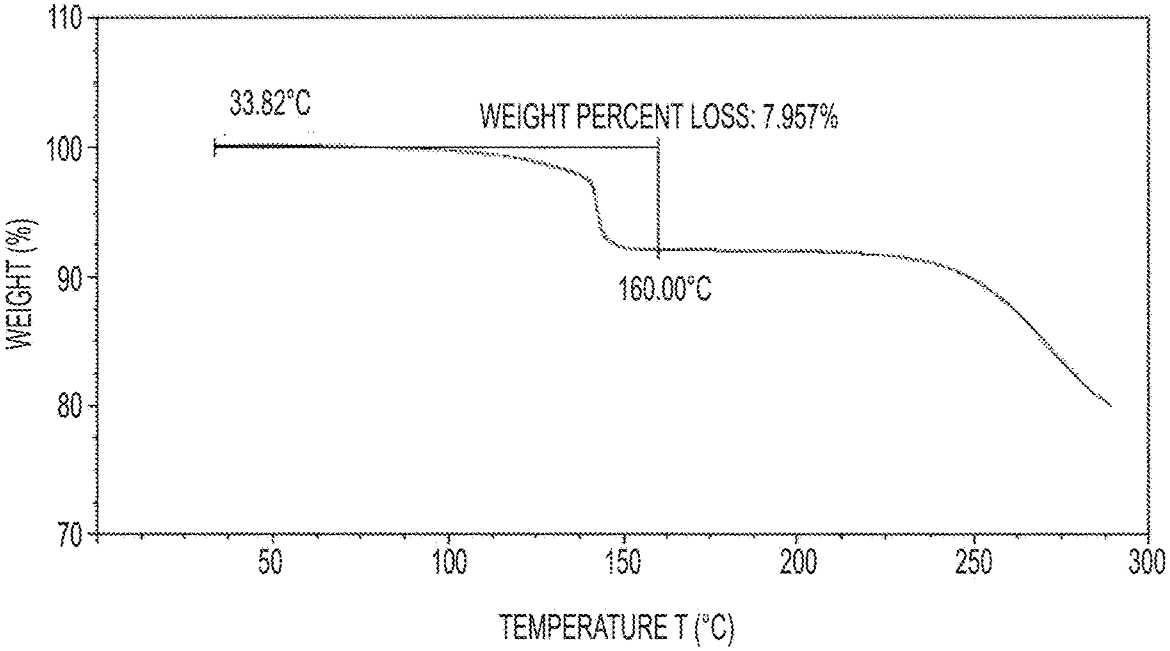
FIG. 19. Illustrates a TGA thermogram of crystalline (S)-2-((2-(2,6-difluoro-4-(methylcarbamoyl)phenyl)-7-methylimidazo[1,2-a]pyridin-3-yl)methyl)morpholine-4-carboxylate (Compound 1), Type B.
Figure 20:
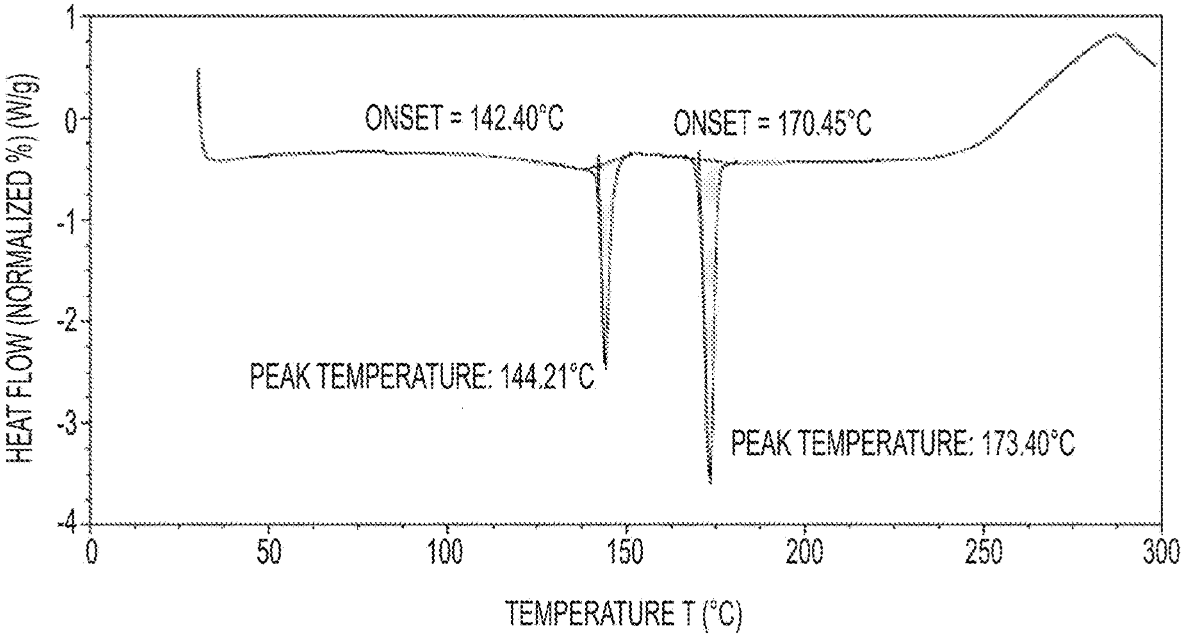
FIG. 20. Illustrates a DSC thermogram of crystalline (S)-2-((2-(2,6-difluoro-4-(methylcarbamoyl)phenyl)-7- methylimidazo[1,2-a]pyridin-3-yl)methyl)morpholine-4-carboxylate (Compound 1), Type B.

In some embodiments, the crystalline form of Compound 1 is crystalline Type B. In some embodiments, Crystalline Type B of Compound 1 is an ethyl acetate solvate characterized as having at least one of the following properties:

(a) an X-ray powder diffraction (XRPD) pattern substantially the same as shown in FIG. 18;

(b) an X-ray powder diffraction (XRPD) pattern with characteristic peaks at about 6.4° 2-Theta, 12.7° 2-Theta, 18.1° 2-Theta, 19.1° 2-Theta, 21.2° 2-Theta, and 23.7° 2-Theta;

(c) a thermo-gravimetric analysis (TGA) substantially similar to the one set forth in FIG. 19;

(d) a DSC thermogram substantially similar to the one set forth in FIG. 20;

(e) a DSC thermogram with two endotherms at about 142° C. and 170° C.; or (f) combinations thereof.

In some embodiments, crystalline Compound 1, Type B, is characterized as having at least two of the properties selected from (a) to (e). In some embodiments, crystalline Compound 1, Type B, is characterized as having at least three of the properties selected from (a) to (e). In some embodiments, crystalline Compound 1, Type B, is characterized as having at least four of the properties selected from (a) to (e). In some embodiments, crystalline Compound 1, Type B, is characterized as having properties (a) to (e).

In some embodiments, crystalline Compound 1, Type B, has an X-ray powder diffraction (XRPD) pattern substantially the same as shown in FIG. 18. In some embodiments, crystalline Compound 1, Type B, has an X-ray powder diffraction (XRPD) pattern with characteristic peaks at about 6.6° 2-Theta, 12.9° 2-Theta, 19.3° 2-Theta, 21.4° 2-Theta, and 23.5° 2-Theta. In some embodiments, crystalline Compound 1, Type B, has a thermo-gravimetric analysis (TGA) thermogram substantially similar to the one set forth in FIG. 19. In some embodiments, crystalline Compound 1, Type B, has a DSC thermogram substantially similar to the one set forth in FIG. 20. In some embodiments, crystalline Compound 1, Type B, has a DSC thermogram with two endotherms at about 142° C. and 170° C.

In some embodiments, the crystalline form of Compound 1 is crystalline Type B. In some embodiments, the crystalline form of Compound 1 is crystalline Type C. In some embodiments, the crystalline form of Compound 1 is crystalline Type D. In some embodiments, the crystalline form of Compound 1 is crystalline Type E. In some embodiments, the crystalline form of Compound 1 is crystalline Type F. In some embodiments, the crystalline form of Compound 1 is crystalline Type G. In some embodiments, the crystalline form of Compound 1 is crystalline Type I. In some embodiments, the crystalline form of Compound 1 is crystalline Type J. In some embodiments, the crystalline form of Compound 1 is crystalline Type L. In some embodiments, the crystalline form of Compound 1 is crystalline Type M.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene.

Class 3 solvents, which possess low toxicity, include: acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1 comprise an organic solvent(s). In some embodiments, compositions comprising Compound 1 comprise a residual amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine. In some embodiments, the Class 3 solvent is selected from the group consisting of acetone, ethyl acetate, isopropyl acetate, tert-butyl methyl ether, heptane, isopropanol, and ethanol.

In some embodiments, compositions comprising Compound 1 comprise a residual amount of a Class 2 solvent. In some embodiments, the organic solvent is a Class 2 solvent. In some embodiments, the Class 2 solvent is selected from the group consisting of acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene. In some embodiments, the Class 2 solvent is selected from the group consisting of acetonitrile, tetrahydrofuran, and toluene. In some embodiments, the Class 2 solvent is acetonitrile.

In some embodiments, compositions comprising Compound 1 comprise a residual amount of a solvent for which no adequate toxicological data were found. In some embodiments, the organic solvent is a solvent for which no adequate toxicological data were found. In some embodiments, the solvent is selected from the group consisting of 2-butanone and 2-methyltetrahydrofuran.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1 is absorbed into the general circulation when the pharmaceutical composition is taken orally as compared to intravenous injection.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1 may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. As an example, one can determine such prophylactically effective amounts by a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, $EC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

In some embodiments described herein is a pharmaceutical composition comprising a crystalline form of Compound 1 and at least one inactive ingredient selected from pharmaceutically acceptable carriers, diluents, and excipients. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 comprises the Type A* family of crystalline forms selected from the group consisting of Type A0, Type A, Type A1, Type A2, and Type A3. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 comprises the Type A* family of crystalline forms selected from the group consisting of Type A0, Type A, and Type A1. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type A0, Type A, Type A1, Type A2, and Type A3. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type A0. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type A. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type A1. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type A2. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type A3. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type K. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type N. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type O. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type B. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type C. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type D. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type E. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type F. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type G. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type I. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type J. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type L. In some embodiments described herein is a pharmaceutical composition comprising a crystalline form of Compound 1 and at least one inactive ingredient selected from pharmaceutically acceptable carriers, diluents, and excipients, wherein the crystalline form of Compound 1 is Type M.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999), herein incorporated by reference in their entirety.

A pharmaceutical composition, as used herein, refers to a mixture of Compound 1 with other chemical components, such as carriers, stabilizers, diluents, dispersing agents, suspending agents, thickening agents, and/or excipients. The pharmaceutical composition facilitates administration of the compound to a mammal. In practicing the methods of treatment or use provided herein, therapeutically effective amounts of Compound 1 are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, and a co-agent, are both administered to a patient simultaneously in the form of a single entity or dosage. The term "non-fixed combination" means that the active ingredients, e.g. Compound 1, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

In some embodiments, crystalline Compound 1 is incorporated into pharmaceutical compositions to provide solid oral dosage forms. In other embodiments, crystalline Compound 1 is used to prepare pharmaceutical compositions other than oral solid dosage forms. The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal, or transdermal administration routes. As used herein, the term "subject" is used to mean an animal, preferably a mammal, including a human or non-human. The terms patient and subject may be used interchangeably.

Moreover, the pharmaceutical compositions described herein, which include Compound 1 can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

The pharmaceutical solid dosage forms described herein can include Compound 1, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of Compound 1. In one embodiment, some or all of the particles of the Compound 1 are coated. In another embodiment, some or all of the particles of the Compound 1 are microencapsulated. In still another embodiment, the particles of the Compound 1 are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol, and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the Compound 1 from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose) (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as calcium, magnesium, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non water-soluble diluent" represents compounds typically used in the formulation of pharmaceuticals, such as calcium phosphate, calcium sulfate, starches, modified starches, microcrystalline cellulose, microcellulose (e.g., having a density of about 0.45 $g/cm^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

A capsule may be prepared, for example, by placing the bulk blend of the formulation of Compound 1 inside of a capsule. In some embodiments, the formulations (non-aqueous suspensions and solutions) are placed in a soft gelatin capsule. In some embodiments, the formulations (non-aqueous suspensions and solutions) are placed in a hard shell gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1 and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

In other embodiments, a powder including the formulations with Compound 1 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

In some embodiments, pharmaceutical formulations are provided that include particles of Compound 1 and at least one dispersing agent or suspending agent for oral administration to a subject. The formulations may be a powder and/or granules for suspension and, upon admixture with water, a substantially uniform suspension is obtained.

It is to be appreciated that there is overlap between the above-listed additives used in the pharmaceutical formulations described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Methods

In some embodiments, described herein is a method for treating a disorder associated with P2X3 activity in a mammal in need thereof, comprising administering to the mammal in need thereof a therapeutically effective amount of a crystalline form of Compound 1 described herein. In some embodiments, described herein is a method for treating pain in a mammal in need thereof, comprising administering to the mammal in need thereof a therapeutically effective amount of a crystalline form of Compound 1 described herein. In some embodiments, described herein is a method for treating a urinary tract disorder in a mammal in need thereof, comprising administering to the mammal in need thereof a therapeutically effective amount of a crystalline form of Compound 1 described herein. In some embodiments is a method for treating a urinary tract disorder in a mammal in need thereof, comprising administering to the mammal in need thereof a therapeutically effective amount of a crystalline form of Compound 1 described herein. In some embodiments is a method for treating a urinary tract disorder in a mammal in need thereof, comprising administering to the mammal in need thereof a therapeutically effective amount of a crystalline form of Compound 1 described herein, wherein the urinary tract disorder comprises an overactive bladder. In some embodiments is a method for treating a urinary tract disorder in a mammal in need thereof, comprising administering to the mammal in need thereof a therapeutically effective amount of a crystalline form of Compound 1 described herein, wherein the urinary tract disorder comprises neurogenic overactive bladder, non-neurogenic overactive bladder, interstitial cystitis, prostatitis, prostadynia, and benign prostatic hyperplasia.

In another aspect, described herein is a method of reducing or preventing uncontrolled loss of urine in a mammal in need thereof, comprising administering to the mammal in need thereof a therapeutically effective amount of a crystalline form of Compound 1 described herein. In some embodiments is a method of reducing or preventing uncontrolled loss of urine in a mammal in need thereof, comprising administering to the mammal in need thereof a therapeutically effective amount of a crystalline form of Compound 1 described herein, wherein the uncontrolled loss of urine is associated with urge incontinence, cough incontinence, stress incontinence, overflow incontinence, functional incontinence, neurogenic incontinence, post-prostatectomy incontinence, urinary urgency, nocturia, and enuresis.

In some embodiments, described herein is a method for treating cough in a mammal in need thereof, comprising administering to the mammal in need thereof a therapeutically effective amount of a crystalline form of Compound 1 described herein. In some embodiments is a method for treating cough in a mammal in need thereof, comprising administering to the mammal in need thereof a therapeutically effective amount of a crystalline form of Compound 1 described herein, wherein the cough is chronic cough. In some embodiments is a method for treating cough in a mammal in need thereof, comprising administering to the mammal in need thereof a therapeutically effective amount of a crystalline form of Compound 1 described herein, wherein the cough is an acute cough. In some embodiments is a method for treating cough in a mammal in need thereof, comprising administering to the mammal in need thereof a therapeutically effective amount of a crystalline form of Compound 1 described herein, wherein the cough is associated with a disease, disorder, or condition selected from chronic obstructive pulmonary disease, asthma, tuberculosis, bronchitis, bronchiectasis, suppurative pulmonary disease, respiratory malignancies, allergy, cystic fibrosis, pulmonary fibrosis, respiratory tract inflammation, emphysema, pneumonia, lung cancer, lung neoplasia, sore throat, common cold, influenza, respiratory tract infection, bronchoconstriction, sarcoidosis, viral or bacterial infection of the upper airways, angiotension converting enzyme (ACE) inhibitor therapy, smoker's cough, chronic non-productive cough, neoplastic cough, cough due to gastroesophageal reflux, and inhalation of irritants, smoke, smog, dust, or air pollution.

In another aspect, described herein is a method for treating pruritus in a mammal in need thereof, comprising administering to the mammal in need thereof a therapeutically effective amount of a crystalline form of Compound 1 described herein. In some embodiments is a method for treating pruritus in a mammal in need thereof, comprising administering to the mammal in need thereof a therapeutically effective amount of a crystalline form of Compound 1 described herein, wherein the pruritus is associated with an inflammatory skin disease, an infectious skin disease, an autoimmune skin disease, or a pregnancy-related skin disease. In some embodiments is a method for treating pruritus in a mammal in need thereof, comprising administering to the mammal in need thereof a therapeutically effective amount of a crystalline form of Compound 1 described herein, wherein the pruritus is associated with an inflammatory skin disease. In some embodiments is a method for treating pruritus in a mammal in need thereof, comprising administering to the mammal in need thereof a therapeutically effective amount of a crystalline form of Compound 1 described herein, wherein the pruritus is associated with an inflammatory skin disease selected from the group consisting of atopic dermatitis, allergic, irritant contact dermatitis, exsiccation dermatitis, nummular and dyshidrotic dermatitis, lichen planus, lichen sclerosus et atrophicus, polymorphous light eruption psoriasis, Grover's disease, mucinosis, mastocytosis, and urticaria. In some embodiments is a method for treating pruritus in a mammal in need thereof, comprising administering to the mammal in need thereof a therapeutically effective amount of a crystalline form of Compound 1 described herein, wherein the pruritus is associated with an infectious skin disease. In some embodiments is a method for treating pruritus in a mammal in need thereof, comprising administering to the mammal in need thereof a therapeutically effective amount of a crystalline form of Compound 1 described herein, wherein the pruritus is associated with an infectious skin disease selected from the group consisting of mycoses, bacterial and viral infections, scabies, pediculosis, insect bites, and folliculitides. In some embodiments is a method for treating pruritus in a mammal in need thereof, comprising administering to the mammal in need thereof a therapeutically effective amount of a crystalline form of Compound 1 described herein, wherein the pruritus is associated with an autoimmune skin disease. In some embodiments is a method for treating pruritus in a mammal in need thereof, comprising administering to the mammal in need thereof a therapeutically effective amount of a crystalline form of Compound 1 described herein, wherein the pruritus is associated with an autoimmune skin disease selected from the group consisting of dermatitis herpetiformis (Duhring's disease), bullous pemphigoid; genodermatoses, Darier's disease, and Hailey-Hailey disease. In some embodiments is a method for treating pruritus in a mammal in need thereof, comprising administering to the mammal in need thereof a therapeutically effective amount of a crystalline form of Compound 1 described herein, wherein the pruritus is associated with a pregnancy-related skin disease. In some embodiments is a method for treating pruritus in a mammal in need thereof, comprising administering to the mammal in need thereof a therapeutically effective amount of a crystalline form of Compound 1 described herein, wherein the pruritus is associated with a pregnancy-related skin disease selected from the group consisting of polymorphic eruption of pregnancy (PEP), atopic eruption of pregnancy, pemphigoid gestationis, neoplasias, and cutaneous T-cell lymphoma. In some embodiments is a method for treating pruritus in a mammal in need thereof, comprising administering to the mammal in need thereof a therapeutically effective amount of a crystalline form of Compound 1 described herein, wherein the pruritus is associated with prurigo nodularis. In some embodiments is a method for treating pruritus in a mammal in need thereof, comprising administering to the mammal in need thereof a therapeutically effective amount of a crystalline form of Compound 1 described herein, wherein the pruritus is associated with a kidney disease or a therapeutic procedure to treat a kidney disease. In some embodiments is a method for treating pruritus in a mammal in need thereof, comprising administering to the mammal in need thereof a therapeutically effective amount of a crystalline form of Compound 1 described herein, wherein the pruritus is associated with a chronic kidney disease. In some embodiments is a method for treating pruritus in a mammal in need thereof, comprising administering to the mammal in need thereof a therapeutically effective amount of a crystalline form of Compound 1 described herein, wherein the pruritus is associated with a therapeutic procedure to treat a kidney disease, wherein the therapeutic procedure to treat the kidney disease is selected from the group consisting of hemodialysis and peritoneal dialysis. In some embodiments is a method for treating pruritus in a mammal in need thereof, comprising administering to the mammal in need thereof a therapeutically effective amount of a crystalline form of Compound 1 described herein, wherein the pruritus is associated with a medical procedure or treatment. In some embodiments is a method for treating pruritus in a mammal in need thereof, comprising administering to the mammal in need thereof a therapeutically effective amount of a crystalline form of Compound 1 described herein, wherein the pruritus is associated with a medical treatment with a drug selected from the group consisting of opioids, anti-malarial drugs, anti-cancer therapies and epidermal growth factor receptor inhibitors.

In another aspect, described herein is a method for treating endometriosis, endometriosis-associated pain, and endometriosis-associated symptoms in a mammal in need thereof, comprising administering to the mammal in need thereof a therapeutically effective amount of a crystalline form of Compound 1 described herein. In some embodiments is a method for treating endometriosis in a mammal in need thereof, comprising administering to the mammal in need thereof a therapeutically effective amount of a crystalline form of Compound 1 described herein. In some embodiments is a method for treating endometriosis-associated pain in a mammal in need thereof, comprising administering to the mammal in need thereof a therapeutically effective amount of a crystalline form of Compound 1 described herein. In some embodiments is a method for treating endometriosis-associated symptoms in a mammal in need thereof, comprising administering to the mammal in need thereof a therapeutically effective amount of a crystalline form of Compound 1 described herein. In some embodiments is a method for treating endometriosis-associated symptoms in a mammal in need thereof, comprising administering to the mammal in need thereof a therapeutically effective amount of a crystalline form of Compound 1 described herein, wherein the endometriosis-associated symptoms are selected from dysmenorrhea, dyspareunia, dysuria, and dyschezia.

Methods of Dosing and Treatment Regimens

The compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder, or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered, if necessary. Subsequently, the dosage or the frequency of administration, or both, can be reduced, as a function of the symptoms, to a level at which the improved disease, disorder, or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

Crystalline forms of Compound 1 described herein, and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In some embodiments, the one or more additional pharmaceutical agents are selected from the group consisting of antihistamines, including but not limited to antihistamines that inhibit action at the histamine $H_1$ receptor (e.g., acrivastine, antazoline, azelastine, bilastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, dexchlorpheniramine, dimenhydrinate, dimetindene, diphenhydramine, doxepin, doxylamine, ebastine, embramine, fexofenadine, hydroxyzine, levocetirizine, loratadine, meclozine, mepyramine, mirtazapine, olopatadine, orphenadrine, phenindamine, pheniramine, phenyltoloxamine, promethazine, pyrilamine, quetiapine, rupatadine, tripelennamine and triprolidine), and antihistamines that inhibit action at the histamine $H_4$ receptor (e.g., thioperamide, JNJ 7777120 and VUF-6002), and analogs and derivatives thereof; serotonin receptor antagonists, including but not limited to 5-$HT_2$ antagonists (e.g., clozapine, cyproheptadine, ketanserin, pizotifen and quetiapine) and 5-$HT_3$ antagonists (e.g., alosetron, cilansetron, dolasetron, granisetron, ondansetron, palonosetron and tropisetron), and analogs and derivatives thereof; neurokinin-1 (NK-1) receptor antagonists, including but not limited to serlopitant, aprepitant, casopitant (GW679769), dapitant, ezlopitant, fosaprepitant, lanepitant (LY-303870), maropitant, netupitant, nolpitant, orvepitant, rolapitant, vestipitant, vofopitant, AV-818, BIIF 1149CL, CP122,721, DNK-333, GSK-424887, L-733060, L-759274, LY-686017, M516102, and TA-5538, and analogs and derivatives thereof; opioid receptor antagonists, including but not limited to butorphanol, cyprodime, levallorphan (lorfan or naloxiphan), nalbuphine, nalorphine (lethidrone or nalline), naloxone, naloxol, nalmefene, naltrexone (e.g., naltrexone 1% cream) and naltrexol, and analogs and derivatives thereof; opioid receptor agonists, including but not limited to selective kappa opioid receptor agonists (e.g., asimadoline, bremazocine, dynorphin, enadoline, ketazocine, nalfurafine, salvinorin A, 2-methoxymethyl salvinorin B, 2-ethoxymethyl salvinorin B, 2-fluoroethoxymethyl salvinorin B, spiradoline, tifluadom, BRL-52537, FE 200665, GR-89696, HZ-2, ICI-199,441, ICI-204,448, LPK-26, U-50488 and U-69,593), and analogs and derivatives thereof; Janus kinase (JAK) inhibitors, including but not limited to JAK1 inhibitors (e.g., GLPG0634 and GSK2586184), JAK2 inhibitors (e.g., lestaurtinib, pacritinib, CYT387 and TG101348), JAK1/JAK2 inhibitors (e.g., baricitinib and ruxolitinib), and JAK3 inhibitors (e.g., tofacitinib), and analogs and derivatives thereof; immunomodulators and immunosuppressants, including but not limited to thalidomide, antimetabolites (e.g., antifolates such as methotrexate), and calcineurin inhibitors (e.g., ciclosporin [cyclosporin], pimecrolimus and tacrolimus), and analogs and derivatives thereof; antidepressants, including but not limited to tricyclic antidepressants (e.g., amitriptyline, amitriptylinoxide, amoxapine, dosulepin [dothiepin], doxepin and melitracen), tetracyclic antidepressants (e.g., amoxapine, maprotiline, mazindol, mianserin, mirtazapine and setiptiline), selective serotonin reuptake inhibitors (SSRIs, e.g., citalopram, dapoxetine, escitalopram, fluoxetine, fluvoxamine, paroxetine and sertraline), and serotonin-norepinephrine reuptake inhibitors (SNRIs, e.g., bicifadine, duloxetine, milnacipran, levomilnacipran, sibutramine, venlafaxine, desvenlafaxine and SEP-227162), and analogs and derivatives thereof; anticonvulsants, including but not limited to carbamazepine, gabapentin, pregabalin, and valproic acid and salts thereof (e.g., sodium valproate), and analogs and derivatives thereof; corticosteroids, including but not limited to hydrocortisone types (e.g., cortisone and derivatives thereof [e.g., cortisone acetate], hydrocortisone and derivatives thereof [e.g., hydrocortisone acetate, hydrocortisone-17-aceponate, hydrocortisone-17-buteprate, hydrocortisone-17-butyrate and hydrocortisone-17-valerate], prednisolone, methylprednisolone and derivatives thereof [e.g., methylprednisolone aceponate], prednisone, and tixocortol and derivatives thereof [e.g., tixocortol pivalate]), betamethasone types (e.g., betamethasone and derivatives thereof [e.g., betamethasone dipropionate, betamethasone sodium phosphate and betamethasone valerate], dexamethasone and derivatives thereof [e.g., dexamethasone sodium phosphate], and fluocortolone and derivatives thereof [e.g., fluocortolone caproate and fluocortolone pivalate]), halogenated steroids (e.g., alclometasone and derivatives thereof [e.g., alclometasone dipropionate], beclometasone and derivatives thereof [e.g., beclometasone dipropionate], clobetasol and derivatives thereof [e.g., clobetasol-17-propionate], clobetasone and derivatives thereof [e.g., clobetasone-17-butyrate], desoximetasone and derivatives thereof [e.g., desoximetasone acetate], diflorasone and derivatives thereof [e.g., diflorasone diacetate], diflucortolone and derivatives thereof [e.g., diflucortolone valerate], fluprednidene and derivatives thereof [e.g., fluprednidene acetate], fluticasone and derivatives thereof [e.g., fluticasone propionate], halobetasol [ulobetasol] and derivatives thereof [e.g., halobetasol proprionate], halometasone and derivatives thereof [e.g., halometasone acetate], and mometasone and derivatives thereof [e.g., mometasone furoate]), acetonides and related substances (e.g., amcinonide, budesonide, ciclesonide, desonide, fluocinonide, fluocinolone acetonide, flurandrenolide [flurandrenolone or fludroxycortide], halcinonide, triamcinolone acetonide and triamcinolone alcohol), and carbonates (e.g., prednicarbate), and analogs and derivatives thereof; local anesthetics, including but not limited to amides (e.g., articaine, bupivacaine, cinchocaine [dibucaine], etidocaine, levobupivacaine, lidocaine [e.g., lidocaine 2.5-5% cream], prilocaine [e.g., prilocaine 2.5% cream], EMLA [lidocaine 2.5%/prilocaine 2.5% cream], mepivacaine, ropivacaine and trimecaine), esters (e.g., benzocaine, chloroprocaine, cocaine, cyclomethycaine, dimethocaine [larocaine], piperocaine, procaine [novocaine], proparacaine, propoxycaine, stovaine and tetracaine [amethocaine]), ethers (e.g., polidocanol [e.g., polidocanol 3% foam] and pramocaine [pramoxine] [e.g., pramoxine 1% cream]), and naturally derived local anesthetics (e.g., cocaine, eugenol, menthol, saxitoxin, neosaxitoxin and tetrodotoxin), and analogs and derivatives thereof; counterirritants and cooling agents, including but not limited to capsaicin, camphor, mint oil, menthol (e.g., menthol 1-3% cream), and phenol (e.g., in calamine lotion), and analogs and derivatives thereof; moisturizers, including but not limited to aqueous moisturizers, low pH moisturizers containing an acid (e.g., lactic acid), and moisturizers containing a humectant that attracts and retains water (e.g., glycerol, sorbitol, lactate, urea, and hyaluronic acid and salts thereof), an occlusive that prevents evaporation {e.g., oils (e.g., mineral oil and silicone oil [e.g., dimethicone]) and petroleum jelly (petrolatum)}, and/or an emollient that provides partial hydration and occlusion (e.g., oils, waxes [e.g., lanolin and paraffin], lipids [e.g., phospholipids, ceramides, triglycerides, glycol stearate, glyceryl stearate, fatty acids and squalene], and sterols [e.g., cholesterol and phytosterol]), and analogs and derivatives thereof; and other kinds of antipruritic agents, including but not limited to S-adenosyl methionine, botulinum toxin (e.g., botulinum toxin types A and B), vitamin D and analogs and derivatives thereof (e.g., calcitriol and calcipotriol [calcipotriene]), non-steroidal anti-inflammatory drugs (NSAIDs, e.g., aspirin), cannabinoid receptor agonists (e.g., CB2 agonists, such as palmitoylethanolamide), inhibitors of cytokines (e.g., antibodies to interleukins, such as IL-31), antagonists of the prostaglandin D2 receptor (DPi) and/or the chemoattractant receptor homologous molecule expressed on TH2 cells (CRTH2) (e.g., TS-022), phosphodiesterase (PDE) inhibitors (e.g., PDE4 inhibitors, such as apremilast), protease-activated receptor 2 (PAR2) antagonists (e.g., GB83), transient receptor potential vanilloid (TRPV) antagonists (e.g., TRPV1 antagonists, such as capsazepine and SB-705498), inhibitors of neurotrophic tyrosine kinase receptors (e.g., TrkA inhibitors, such as CT327), antimicrobials (including antibiotics, antifungals, antivirals and antiparasitics, such as crotamiton and rifampin [rifampicin]), bile absorption-reducing or bile sequestering agents (e.g., ursodeoxycholic acid [ursodiol]), ultraviolet radiation (e.g., ultraviolet A and B), and therapeutic agents that treat the underlying causes of the pruritus-associated conditions, and analogs and derivatives thereof.

In some embodiments, the one or more additional pharmaceutical agents is an NK-1 antagonist wherein the NK-1 antagonist is selected from the group consisting of, but not limited to serlopitant, aprepitant, casopitant, dapitant, ezlopitant, fosaprepitant, lanepitant, maropitant, netupitant, nolpitant, orvepitant, rolapitant, vestipitant, vofopitant, AV-818, BIIF 1149CL, CP122,721, DNK-333, GSK-424887, L-733060, L-759274, LY-686017, M516102, and TA-5538, and analogs and derivatives thereof. In some embodiments, the NK-1 antagonist is selected from the group consisting of serlopitant, orvepitant, rolapitant, aprepitant, and fosaprepitant, or a pharmaceutically acceptable salt thereof. In some embodiments, the NK-1 antagonist is serlopitant, or a pharmaceutically acceptable salt thereof. In some embodiments, the NK-1 antagonist is orvepitant, or a pharmaceutically acceptable salt thereof. In some embodiments, the NK-1 antagonist is rolapitant, or a pharmaceutically acceptable salt thereof. In some embodiments, the NK-1 antagonist is aprepitant, or a pharmaceutically acceptable salt thereof. In some embodiments, the NK-1 antagonist is fosaprepitant, or a pharmaceutically acceptable salt thereof.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

EXAMPLES

List of Abbreviations

As used throughout the description of the invention, the following abbreviations, unless otherwise indicated, shall be understood to have the following meanings:

| | |
|---|---|
| ACN or MeCN | acetonitrile |
| Bn | benzyl |
| BOC or Boc | tert-butyl carbamate |
| t-Bu | tert-butyl |
| Cy | cyclohexyl |
| DCE | dichloroethane ($ClCH_2CH_2Cl$) |
| DCM | dichloromethane ($CH_2Cl_2$) |
| DIPEA or DIEA | diisopropylethylamine |
| DMAP | 4-(N,N-dimethylamino)pyridine |
| DMF | dimethylformamide |
| DMA | N,N-dimethylacetamide |
| DMSO | dimethylsulfoxide |

-continued

| | |
|---|---|
| eq or equiv | equivalent(s) |
| Et | ethyl |
| $Et_2O$ | diethyl ether |
| EtOH | ethanol |
| EtOAc | ethyl acetate |
| GC | gas chromatography |
| h | hour(s) |
| HPLC | high performance liquid chromatography |
| IPA | isopropyl alcohol |
| IPAc | isopropyl acetate |
| KF | Karl Fischer |
| Me | methyl |
| MeOH | methanol |
| MS | mass spectroscopy |
| MEK | methyl ethyl ketone |
| MIBK | methyl isobutyl ketone |
| MTBE | methyl t-butyl ether |
| min | minutes |
| MsOH | methanesulfonic acid |
| NMR | nuclear magnetic resonance |
| RP-HPLC | reverse phase-high performance liquid chromatography |
| RT | room temperature |
| TFA | trifluoroacetic acid |
| THF | tetrahydrofuran |
| TLC | thin layer chromatography |

Example 1: Preparation of Compound 1

The preparation of Compound 1 is disclosed in U.S. Pat. No. 9,598,409, the content of which is incorporated by reference in its entirety.

Example 2: Polymorph Screen of Compound 1

Approximate solubility of starting material (Compound 1, Form A0) was determined in 28 solvents at RT (25±3° C.). ~2 mg of the starting material was added into each 3-mL glass vial. Solvents were then added stepwise (50/50/200/700 μL per step) into the vials until the solids were dissolved visually or a total volume of 1 mL was reached. Solubility results summarized in Table 2 were used to guide the solvent selection in screening design.

TABLE 2

| Solvent | Solubility (mg/mL) | Solvent | Solubility (mg/mL) |
|---|---|---|---|
| DMSO | S > 48.0 | MEK | 7.7 < S < 23.0 |
| EtOH | S > 46.0 | Diethyleneglycol | 2.4 < S < 8.0 |
| THF | S > 46.0 | 1,4-Dioxane | 2.4 < S < 8.0 |
| MeOH | S > 44.0 | Anisole | 2.0 < S < 6.7 |
| n-Butanol | S > 42.0 | 2-MeTHF | 1.8 < S < 6.0 |
| $CHCl_3$ | S > 40.0 | $H_2O$ | S < 2.4 |
| DCM | S > 40.0 | Butyl acetate | S < 2.4 |
| DMF | S > 38.0 | MIBK | S < 2.2 |
| 1-Propanol | S > 38.0 | MTBE | S < 2.2 |
| 1,2-Dichloroethane | S > 38.0 | n-Hexane | S < 2.2 |
| ACN | 20.0 < S < 40.0 | EtOAc | S < 2.0 |
| IPA | 20.0 < S < 40.0 | Toluene | S < 2.0 |
| Acetone | 19.0 < S < 38.0 | IPAc | S < 1.9 |
| Dimethoxyethane | 6.7 < S < 20.0 | n-Heptane | S < 1.9 |

Polymorph screening experiments were performed using different crystallization or solid transition methods.

Example 2A: Polymorph Screen—Slurry at Room Temperature

Twenty-four slurry conversion experiments were conducted at RT in different solvent systems. About 15 mg of Compound 1 starting material was suspended in 0.3 mL of the corresponding solvent in an HPLC vial. After the suspensions were magnetically stirred at RT for 5 days, the residual solids were isolated for XRPD analysis. Results are shown in Table 3 and indicated that Type A* family, Types B~G, I, J, M, N and amorphous sample were obtained.

TABLE 3

| Solvent (v/v) | Solid form |
|---|---|
| DMSO/$H_2O$ (1:1) | Amorphous |
| EtOH/n-Heptane (1:1) | Type M |
| THF/$H_2O$ (1:1) | Type A* family |
| $CHCl_3$/n-Hexane (1:1) | Type B |
| DCM/n-Heptane (1:1) | Type A* family |
| n-Butanol/$H_2O$ (1:1) | Amorphous |
| ACN | Type A* family |
| IPA | Type G |
| Acetone | Type B |
| 1,4-Dioxane | Type E |
| Anisole | Type I |

TABLE 3-continued

| Solvent (v/v) | Solid form |
|---|---|
| 2-MeTHF | Type C |
| $H_2O$ | Type A* family |
| MIBK | Type D |
| MTBE | Type J |
| EtOAc | Type B |
| Toluene | Type I |
| Butyl acetate | Type N |
| MeOH | Type A* family |
| MEK | Type F |
| MeOH/$H_2O$ (937:63, aw = 0.2) | Type A* family |
| MeOH/$H_2O$ (844:156, aw = 0.4) | Type A* family |
| MeOH/$H_2O$ (696:304, aw = 0.6) | Type A* family |
| MeOH/$H_2O$ (418:582, aw = 0.8) | Type A* family |

Example 2B: Polymorph Screen—Slurry at 50° C.

Fifteen slurry conversion experiments were conducted at 50° C. in different solvent systems. About 20 mg of Compound 1 starting material was suspended in 0.2 mL of the corresponding solvent in an HPLC vial. After the suspensions were magnetically stirred at 50° C. for about 5 days, the residual solids were isolated for XRPD analysis. Results are shown in Table 4 and indicated that Type A* family, Types B~F, I, J, K, and M were obtained.

TABLE 4

| Solvent(v/v) | Solid form |
|---|---|
| MeOH | Type A* family |
| l-Propanol/$H_2O$ (1:1) | Type M |
| Acetone/$H_2O$ (1:1) | Type B |
| MEK | Type F |
| MIBK | Type D |
| THF/$H_2O$ (1:1) | Type B |
| 2-MeTHF | Type C |
| 1,2-Dichloroethane/n-Heptane (1:1) | Type A* family + Type B |
| MTBE | Type J |
| EtOAc | Type B |
| Anisole | Type I |
| IPAc | Type K |
| Toluene | Type I |
| $H_2O$ | Type A* family |
| ACN | Type A* family + Type B |

Example 2C: Polymorph Screen—Solid Vapor Diffusion

Solid vapor diffusion experiments were conducted in an atmosphere of 13 different solvents. Approximate 10 mg of Compound 1 starting material was weighed into each 3-mL glass vial, which was then placed into a 20-mL glass vial with 2 mL of the corresponding solvent. The 20-mL glass vial was sealed with a cap and kept at RT allowing sufficient time for solvent vapor to interact with the solids. The residual solids were tested by XRPD. Results are shown in Table 5 and indicated that Type A* family, Types B, J, L, M, and amorphous sample were generated.

TABLE 5

| Solvent | Solid form |
|---|---|
| $H_2O$ | Type A* family |
| DCM | Amorphous |
| EtOH | Type M |
| MeOH | Type A* family |

TABLE 5-continued

| Solvent | Solid form |
|---|---|
| ACN | Type A* family + Type B |
| Dimethoxyethane | Type B |
| $CHCl_3$ | Amorphous |
| Acetone | Type B |
| n-Butanol | Type M |
| EtOAc | Type B |
| MTBE | Type A* family + Type J |
| Diethyleneglycol | Type M |
| DMSO | Type L |

Example 2D: Polymorph Screen—Liquid Vapor Diffusion

Eleven liquid vapor diffusion experiments were conducted. Approximately 15 mg of Compound 1 starting material was dissolved in appropriate solvent to obtain a clear solution in each 3-mL glass vial. The 3-mL glass vial was then placed into a 20-mL glass vial with 3 mL of the corresponding solvent. The 20-mL glass vial was sealed with a cap and kept at RT allowing sufficient time for solvent vapor to interact with the solution. The precipitates were isolated for XRPD analysis. Results are shown in Table 6 and indicated that Type A* family, Types B, D, F, I, J, M, and amorphous sample were generated.

TABLE 6

| Solvent | Anti-solvent | Solid form |
|---|---|---|
| THF | $H_2O$ | Type A* family + Type B |
| THF | MTBE | Type B + J |
| THF | MEK | Type F |
| THF | n-Heptane | Type A* family + Type B |
| ACN | $H_2O$ | Amorphous |
| ACN | MIBK | Type D + J |
| ACN | EtOAc | Type B |
| ACN | Toluene | Amorphous |
| EtOH | Toluene | Type I |
| EtOH | $H_2O$ | Type M |
| EtOH | n-Hexane | Type M |

Example 2E: Polymorph Screen—Slow Evaporation

Slow evaporation experiments were performed under eight conditions. 15 mg of Compound 1 starting material was dissolved in 0.2~1.0 mL of corresponding solvent in each 3-mL glass vial. If complete dissolution was not achieved, suspensions were filtered using a PTFE membrane (pore size of 0.45 μm) and the filtrates were used for the following steps. The visually clear solutions were covered by Parafilm® with 6 pinholes and subjected to evaporation at RT. The precipitates were isolated for XRPD analysis. Results are shown in Table 7 and indicated that Type A* family, Types B, M, and amorphous sample were obtained.

TABLE 7

| Solvent | Solid form |
|---|---|
| DMSO | Type A* family |
| EtOH | Type M |
| MeOH | Type A* family |
| CHCl3 | Amorphous |
| DCM | Type A* family |
| ACN | Type A* family |

TABLE 7-continued

| Solvent | Solid form |
|---|---|
| IPA | Type M |
| Acetone | Type B |

Example 2F: Polymorph Screen—Polymer Induced Crystallization

Polymer-induced crystallization experiments were performed under six conditions. 15 mg of Compound 1 starting material was dissolved in 0.8~3.5 mL of corresponding solvent in each 3-mL glass vial. If complete dissolution was not achieved, suspensions were filtered using a PTFE membrane (pore size of 0.45 μm) and the filtrates were used for the following steps. ~2 mg of polymer mixture A (polyvinyl pyrrolidone (PVP), polyvinyl alcohol (PVA), polyvinylchloride (PVC), polyvinyl acetate (PVAC), hypromellose (HPMC), methyl cellulose (MC); mass ratio of 1:1:1:1:1:1) or polymer mixture B (polycaprolactone (PCL), polyethylene glycol (PEG), poly (methyl methacrylate) (PMMA) sodium alginate (SA), and hydroxyethyl cellulose (HEC); mass ratio of 1:1:1:1:1) was added into the clear solution. The solutions were then covered by Parafilm® with 6 pinholes and subjected to evaporation at RT. The precipitates were isolated for XRPD analysis. Results are shown in Table 8 and indicated that Type A* family, Types B, M, and amorphous sample were obtained.

TABLE 8

| Solvent | Polymer Mixture | Solid form |
|---|---|---|
| Dimethoxyethane | A | Amorphous |
| DCM | A | Type A* family |
| $CHCl_3$ | A | Amorphous |
| Acetone | B | Type B |
| 1-Propanol | B | Type M |
| EtOH | B | Type M |

Example 2G: Polymorph Screen—Slow Cooling

Slow cooling experiments were conducted in eight solvent systems. About 20 mg of Compound 1 starting material was suspended in 1.0 mL of the corresponding solvent in each 3-mL glass vial at RT. The suspensions were then heated to 50° C., equilibrated for about two hours and then filtered using a PTFE membrane (pore size of 0.45 μm). Filtrates were slowly cooled down to 5° C. at a rate of 0.1° C./min. If no solids were obtained during cooling, the solution was then transferred to 5° C./−20° C. or further subjected to evaporation at RT. The solids were isolated for XRPD analysis. Results are shown in Table 9 and indicated that Types B, I, J, and amorphous sample were obtained.

TABLE 9

| Solvent (v/v) | Solid form |
|---|---|
| ACN | Type I |
| IPA | Amorphous |
| Acetone | Type B |
| Dimethoxyethane | Type B |
| Anisole | Type I |

TABLE 9-continued

| Solvent (v/v) | Solid form |
|---|---|
| 2-MeTHF | Type J |
| THF/$H_2O$ (1:1) | Amorphous |
| $CHCl_3$/n-Heptane (1:1) | Type B |

Example 2H: Polymorph Screen—Anti-Solvent Addition

A total of 18 anti-solvent addition experiments were carried out. About 15 mg of Compound 1 starting material was dissolved in 0.05-0.8 mL of the corresponding solvent to obtain a clear solution. The solution was magnetically stirred with addition of 0.2 mL of the corresponding anti-solvent per step until precipitates appeared or the total amount of anti-solvent reached 15.0 mL. The precipitates were isolated for XRPD analysis. Results are shown in Table 10 and indicated that Type A* family, Types B, D, I, J, M, gel sample, and amorphous sample were obtained.

TABLE 10

| Solvent | Anti-solvent | Solid form |
|---|---|---|
| DMSO | $H_2O$ | Type A* family |
| DMSO | EtOAc | Type B |
| 1-Propanol | n-Hexane | Type A* family + Type M |
| 1-Propanol | $H_2O$ | Type A* family |
| THF | Toluene | Type I |
| THF | n-Heptane | Type A* family + Type B |
| MeOH | MIBK | Type D + J |
| MeOH | $H_2O$ | Type A* family |
| n-Butanol | MTBE | Amorphous |
| n-Butanol | IPAc | Amorphous |
| DCM | Toluene | Type I |
| DCM | n-Heptane | Type A* family |
| Acetone | MTBE | Amorphous |
| Acetone | $H_2O$ | Amorphous |
| ACN | $H_2O$ | Amorphous |
| ACN | Toluene | Amorphous |
| 1,2-Dichloroethane | $H_2O$ | Gel |
| 1,2-Dichloroethane | n-Hexane | Type A* family |

Example 3: X-Ray Powder Diffraction (XRPD)

X-ray powder diffraction studies were performed using PANalytical and Bruker X-ray powder diffractometers in reflection mode with the following instrument parameters:

| Parameters | PANalytical | PANalytical | Bruker |
|---|---|---|---|
| Model | Empyrean | X' Pert3 | D2 PHASER |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 | Cu, kα, Kα1 (Å): 1.54060 Kα2 (Å): 1.54439 Kα2/Kα1 intensity ratio: 0.50 |
| X-Ray tube setting | 45 kV, 40 mA | 45 kV, 40 mA | 30 kV, 10 mA |
| Divergence slit | Automatic | 1/8° | 0.6 mm |
| Scan mode | Continuous | Continuous | Continuous |
| Scan range (°2TH) | 3°-40° | 3°-40° | 3°-40° |
| Scan step time (s) | 17.8 | 46.7 | 0.1 |
| Step size (°2TH) | 0.0167 | 0.0263 | 0.0201 |
| Test Time | 5 min 30 s | 5 min 04 s | 3 min 28 s |

XRPD analysis of Compound 1, Type A, (FIG. 1) showed Type A to be crystalline with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta. Compound 1 crystalline form Type A was found to be a channel hydrate, which can accommodate different amounts of water in the crystal lattice depending on the ambient humidity, resulting in slight peak shifts in the XRPD patterns. Four Type A related forms (Type A0, Type A1, Type A02, and Type A3) were found and also shown to be crystalline (FIG. 1). Tables 11-15 show the XRPD peak information for the Type A* family (Type A, Type A0, Type A1, Type A02, and Type A3).

TABLE 11

XRPD Peak List of Compound 1, Type A

| Pos. [°2Th.] | Height [cts] | FWHM Left [°2Th.] | d-spacing [Å] | Rel. Int. [%] |
|---|---|---|---|---|
| 6.937452 | 767.132200 | 0.150552 | 12.74198 | 85.80 |
| 9.157135 | 548.766100 | 0.083640 | 9.65771 | 61.38 |
| 10.917440 | 538.455200 | 0.150552 | 8.10416 | 60.23 |
| 11.289910 | 753.093000 | 0.133824 | 7.83761 | 84.23 |
| 11.506490 | 765.956200 | 0.167280 | 7.69057 | 85.67 |
| 12.801290 | 637.916100 | 0.133824 | 6.91546 | 71.35 |
| 13.748880 | 462.567200 | 0.200736 | 6.44090 | 51.74 |
| 15.979300 | 492.163100 | 0.150552 | 5.54654 | 55.05 |
| 16.265890 | 398.943400 | 0.133824 | 5.44945 | 44.62 |
| 17.303940 | 160.195200 | 0.133824 | 5.12482 | 17.92 |
| 17.804100 | 610.135500 | 0.066912 | 4.98196 | 68.24 |
| 18.375130 | 336.355600 | 0.167280 | 4.82841 | 37.62 |
| 19.046480 | 551.892700 | 0.100368 | 4.65970 | 61.73 |
| 20.203340 | 449.605800 | 0.150552 | 4.39542 | 50.29 |
| 20.742600 | 894.043300 | 0.066912 | 4.28235 | 100.00 |
| 21.591220 | 794.269200 | 0.167280 | 4.11592 | 88.84 |
| 22.569850 | 818.152100 | 0.184008 | 3.93962 | 91.51 |
| 23.839390 | 245.305000 | 0.267648 | 3.73262 | 27.44 |
| 24.609190 | 403.934400 | 0.133824 | 3.61758 | 45.18 |
| 24.916890 | 440.139800 | 0.100368 | 3.57360 | 49.23 |
| 25.380410 | 426.789000 | 0.167280 | 3.50937 | 47.74 |
| 25.796050 | 552.332900 | 0.200736 | 3.45376 | 61.78 |
| 26.750220 | 183.389000 | 0.334560 | 3.33270 | 20.51 |
| 27.864560 | 167.794500 | 0.468384 | 3.20190 | 18.77 |
| 28.705330 | 194.177600 | 0.200736 | 3.11000 | 21.72 |
| 29.383970 | 140.834700 | 0.200736 | 3.03970 | 15.75 |
| 30.970270 | 79.833320 | 0.267648 | 2.88753 | 8.93 |
| 31.871760 | 102.633200 | 0.267648 | 2.80789 | 11.48 |
| 33.743060 | 46.432270 | 0.401472 | 2.65633 | 5.19 |

TABLE 12

XRPD Peak List of Compound 1, Type A0

| Pos. [°2Th.] | Height [cts] | FWHM Left [°2Th.] | d-spacing [Å] | Rel. Int. [%] |
|---|---|---|---|---|
| 7.052154 | 1105.568000 | 0.230256 | 12.53499 | 100.00 |
| 9.226489 | 534.327100 | 0.127920 | 9.58527 | 48.33 |
| 11.011350 | 585.336100 | 0.102336 | 8.03525 | 52.94 |
| 11.398860 | 683.049700 | 0.076752 | 7.76295 | 61.78 |
| 11.567530 | 694.960900 | 0.102336 | 7.65013 | 62.86 |
| 12.518360 | 252.570700 | 0.102336 | 7.07112 | 22.85 |
| 12.897610 | 622.976100 | 0.127920 | 6.86403 | 56.35 |
| 13.813190 | 393.869300 | 0.102336 | 6.41106 | 35.63 |
| 16.029290 | 357.942400 | 0.102336 | 5.52936 | 32.38 |
| 16.375130 | 347.410100 | 0.102336 | 5.41335 | 31.42 |
| 17.924780 | 407.343700 | 0.127920 | 4.94869 | 36.84 |
| 18.473940 | 211.760800 | 0.127920 | 4.80281 | 19.15 |
| 19.118280 | 316.294700 | 0.230256 | 4.64236 | 28.61 |
| 20.254580 | 310.253100 | 0.127920 | 4.38442 | 28.06 |
| 20.779910 | 541.609000 | 0.102336 | 4.27475 | 48.99 |
| 21.554790 | 443.889000 | 0.153504 | 4.12280 | 40.15 |
| 22.602610 | 559.456800 | 0.127920 | 3.93398 | 50.60 |
| 23.869090 | 130.054300 | 0.307008 | 3.72804 | 11.76 |
| 24.701550 | 242.840500 | 0.127920 | 3.60426 | 21.97 |
| 25.037700 | 183.740200 | 0.409344 | 3.55663 | 16.62 |
| 25.509000 | 325.365700 | 0.127920 | 3.49197 | 29.43 |
| 25.943290 | 323.593100 | 0.127920 | 3.43449 | 29.27 |
| 26.843070 | 85.631520 | 0.307008 | 3.32138 | 7.75 |
| 27.895730 | 80.375630 | 0.409344 | 3.19839 | 7.27 |
| 28.850400 | 123.174200 | 0.153504 | 3.09469 | 11.14 |
| 29.552870 | 72.513820 | 0.307008 | 3.02271 | 6.56 |
| 31.889120 | 58.896500 | 0.307008 | 2.80640 | 5.33 |

TABLE 13

XRPD Peak List of Compound 1, Type A1

| Pos. [°2Th.] | Height [cts] | FWHM Left [°2Th.] | d-spacing [Å] | Rel. Int. [%] |
|---|---|---|---|---|
| 6.975453 | 983.788100 | 0.153504 | 12.67265 | 100.00 |
| 9.238976 | 367.891200 | 0.076752 | 9.57234 | 37.40 |
| 11.032450 | 396.125600 | 0.102336 | 8.01993 | 40.27 |
| 11.198830 | 382.825300 | 0.051168 | 7.90115 | 38.91 |
| 11.402110 | 453.023900 | 0.076752 | 7.76074 | 46.05 |
| 11.594000 | 469.564700 | 0.076752 | 7.63272 | 47.73 |
| 11.997660 | 110.675300 | 0.076752 | 7.37681 | 11.25 |
| 12.403510 | 193.732600 | 0.153504 | 7.13634 | 19.69 |
| 12.761300 | 483.940100 | 0.127920 | 6.93705 | 49.19 |
| 13.780000 | 385.573600 | 0.102336 | 6.42643 | 39.19 |
| 15.858990 | 163.012200 | 0.127920 | 5.58835 | 16.57 |
| 16.063160 | 224.952500 | 0.076752 | 5.51777 | 22.87 |
| 16.223450 | 195.285000 | 0.076752 | 5.46362 | 19.85 |
| 16.640570 | 74.625240 | 0.153504 | 5.32759 | 7.59 |
| 17.832800 | 298.942800 | 0.102336 | 4.97401 | 30.39 |
| 18.328770 | 155.649100 | 0.127920 | 4.84052 | 15.82 |
| 18.883300 | 150.673400 | 0.076752 | 4.69960 | 15.32 |
| 19.103560 | 162.358900 | 0.204672 | 4.64591 | 16.50 |

TABLE 13-continued

XRPD Peak List of Compound 1, Type A1

| Pos. [°2Th.] | Height [cts] | FWHM Left [°2Th.] | d-spacing [Å] | Rel. Int. [%] |
|---|---|---|---|---|
| 20.220260 | 232.443600 | 0.127920 | 4.39178 | 23.63 |
| 20.725530 | 614.416600 | 0.127920 | 4.28584 | 62.45 |
| 20.999270 | 287.697300 | 0.102336 | 4.23059 | 29.24 |
| 21.598770 | 509.877700 | 0.153504 | 4.11450 | 51.83 |
| 22.591660 | 537.506800 | 0.127920 | 3.93587 | 54.64 |
| 23.927610 | 112.478200 | 0.204672 | 3.71906 | 11.43 |
| 25.023530 | 322.673300 | 0.153504 | 3.55861 | 32.80 |
| 25.212040 | 416.606600 | 0.127920 | 3.53243 | 42.35 |
| 25.666820 | 383.124100 | 0.102336 | 3.47086 | 38.94 |
| 26.772800 | 109.297100 | 0.127920 | 3.32994 | 11.11 |
| 27.624260 | 78.333130 | 0.409344 | 3.22920 | 7.96 |
| 28.544020 | 114.981800 | 0.102336 | 3.12721 | 11.69 |
| 28.703410 | 57.681500 | 0.818688 | 3.11021 | 5.86 |
| 32.010810 | 21.751020 | 0.511680 | 2.79601 | 2.21 |

TABLE 14

XRPD Peak List of Compound 1, Type A2

| Pos. [°2Th.] | Height [cts] | FWHM Left [°2Th.] | d-spacing [Å] | Rel. Int. [%] |
|---|---|---|---|---|
| 3.106108 | 934.188100 | 0.255840 | 28.44515 | 100.00 |
| 6.858556 | 422.061000 | 0.063960 | 12.88838 | 45.18 |
| 9.242472 | 317.792900 | 0.063960 | 9.56873 | 34.02 |
| 11.090770 | 472.788500 | 0.076752 | 7.97789 | 50.61 |
| 11.429380 | 607.596700 | 0.076752 | 7.74229 | 65.04 |
| 11.623750 | 629.048800 | 0.063960 | 7.61325 | 67.34 |
| 12.561090 | 249.379400 | 0.102336 | 7.04716 | 26.69 |
| 13.744410 | 258.777900 | 0.076752 | 6.44299 | 27.70 |
| 16.067670 | 535.082800 | 0.127920 | 5.51623 | 57.28 |
| 16.394570 | 303.354200 | 0.076752 | 5.40697 | 32.47 |
| 16.643300 | 247.388900 | 0.255840 | 5.32672 | 26.48 |
| 17.660940 | 336.240500 | 0.076752 | 5.02202 | 35.99 |
| 18.124140 | 246.817900 | 0.089544 | 4.89470 | 26.42 |
| 18.692630 | 66.680110 | 0.153504 | 4.74710 | 7.14 |
| 19.159750 | 239.619400 | 0.076752 | 4.63241 | 25.65 |
| 20.160580 | 118.654800 | 0.127920 | 4.40465 | 12.70 |
| 20.668580 | 412.245300 | 0.127920 | 4.29752 | 44.13 |
| 21.284290 | 254.620000 | 0.076752 | 4.17458 | 27.26 |
| 21.574750 | 339.161300 | 0.063960 | 4.11903 | 36.31 |
| 22.555880 | 316.574400 | 0.102336 | 3.94203 | 33.89 |
| 23.846040 | 180.754300 | 0.127920 | 3.73159 | 19.35 |
| 24.649270 | 404.866600 | 0.063960 | 3.61178 | 43.34 |
| 24.986170 | 421.209300 | 0.102336 | 3.56384 | 45.09 |
| 25.283260 | 276.699800 | 0.102336 | 3.52264 | 29.62 |
| 26.064600 | 199.683000 | 0.153504 | 3.41878 | 21.38 |
| 27.222960 | 214.770700 | 0.089544 | 3.27589 | 22.99 |
| 28.070090 | 129.338700 | 0.127920 | 3.17892 | 13.85 |
| 28.978800 | 173.338400 | 0.076752 | 3.08127 | 18.55 |
| 30.324760 | 87.345550 | 0.204672 | 2.94751 | 9.35 |
| 31.642360 | 58.915590 | 0.307008 | 2.82772 | 6.31 |

TABLE 15

XRPD Peak List of Compound 1, Type A3

| Pos. [°2Th.] | Height [cts] | FWHM Left [°2Th.] | d-spacing [Å] | Rel. Int. [%] |
|---|---|---|---|---|
| 6.939484 | 4901.742000 | 0.117096 | 12.73825 | 100.00 |
| 8.626023 | 355.983800 | 0.133824 | 10.25112 | 7.26 |
| 9.083663 | 1384.279000 | 0.150552 | 9.73566 | 28.24 |
| 10.875770 | 1948.399000 | 0.117096 | 8.13511 | 39.75 |
| 11.384440 | 2417.799000 | 0.234192 | 7.77275 | 49.33 |
| 12.383190 | 1855.601000 | 0.133824 | 7.14800 | 37.86 |
| 12.871570 | 3546.026000 | 0.167280 | 6.87787 | 72.34 |
| 13.686800 | 2238.386000 | 0.133824 | 6.46997 | 45.67 |
| 13.961720 | 1340.470000 | 0.117096 | 6.34319 | 27.35 |
| 14.656250 | 386.715400 | 0.200736 | 6.04413 | 7.89 |

TABLE 15-continued

XRPD Peak List of Compound 1, Type A3

| Pos. [°2Th.] | Height [cts] | FWHM Left [°2Th.] | d-spacing [Å] | Rel. Int. [%] |
|---|---|---|---|---|
| 15.849620 | 2240.850000 | 0.150552 | 5.59163 | 45.72 |
| 16.337180 | 2698.021000 | 0.150552 | 5.42584 | 55.04 |
| 17.179710 | 666.603500 | 0.200736 | 5.16159 | 13.60 |
| 17.848540 | 2154.465000 | 0.117096 | 4.96966 | 43.95 |
| 18.454930 | 1284.539000 | 0.133824 | 4.80771 | 26.21 |
| 18.948690 | 2110.082000 | 0.100368 | 4.68353 | 43.05 |
| 20.038030 | 2678.331000 | 0.150552 | 4.43131 | 54.64 |
| 20.619510 | 3175.488000 | 0.167280 | 4.30764 | 64.78 |
| 21.032110 | 3163.758000 | 0.167280 | 4.22406 | 64.54 |
| 21.316330 | 3001.577000 | 0.133824 | 4.16837 | 61.23 |
| 21.789280 | 2057.597000 | 0.133824 | 4.07895 | 41.98 |
| 22.330630 | 3375.890000 | 0.100368 | 3.98128 | 68.87 |
| 23.678990 | 1412.789000 | 0.200736 | 3.75754 | 28.82 |
| 24.740260 | 2165.739000 | 0.334560 | 3.59871 | 44.18 |
| 25.051770 | 2453.556000 | 0.167280 | 3.55466 | 50.05 |
| 25.547240 | 3446.841000 | 0.184008 | 3.48683 | 70.32 |
| 25.989310 | 2957.744000 | 0.167280 | 3.42852 | 60.34 |
| 26.562370 | 1290.737000 | 0.267648 | 3.35584 | 26.33 |
| 27.630080 | 1124.267000 | 0.200736 | 3.22854 | 22.94 |
| 27.942330 | 1265.072000 | 0.133824 | 3.19316 | 25.81 |
| 28.952600 | 1502.745000 | 0.133824 | 3.08400 | 30.66 |
| 29.686600 | 787.233500 | 0.133824 | 3.00940 | 16.06 |
| 31.088340 | 586.889500 | 0.267648 | 2.87683 | 11.97 |
| 31.712030 | 523.747800 | 0.267648 | 2.82166 | 10.68 |
| 34.069700 | 267.460200 | 0.401472 | 2.63160 | 5.46 |
| 36.400380 | 112.813100 | 0.401472 | 2.46828 | 2.30 |

Example 4: Thermogravimetric Analysis (TGA)

TGA data were collected using a Q500/5000 and Discovery 5500 TGA from TA Instruments with the following instrument parameters:

| | |
|---|---|
| Method | Ramp |
| Sample pan | Aluminum, open |
| Temperature | RT-350° C. |
| Heating rate | 10° C./min |
| Purge gas | $N_2$ |

TGA of Compound 1, Type A0, (FIG. 2) showed a weight loss of 1% up to 150° C.

Example 5: Differential Scanning Calorimetry (DSC)

DSC was performed using a Q200/2000 and Discovery 2500 DSC from TA Instruments with the following instrument parameters:

| | |
|---|---|
| Method | Ramp |
| Sample pan | Aluminum, crimped |
| Temperature | 25° C.-300° C. |
| Heating rate | 10° C./min |
| Purge gas | $N_2$ |

DSC result of crystalline Compound 1, Type A0, (FIG. 2) showed a single sharp endothermic peak with an onset at about 167° C.

Example 6: Dynamic Vapor Sorption (DVS)

DVS test was performed using an SMS (Surface Measurement Systems) DVS Intrinsic instrument. The relative humidity were calibrated against deliquescence point of LiCl, $Mg(NO_3)_2$ and KCl. The following instrument parameters were used at 25° C. and 40° C.:

| | 25° C. | 40° C. |
|---|---|---|
| Temperature | 25° C. | 40° C. |
| Sample size | 10~20 mg | 10~20 mg |
| Gas and flow rate | $N_2$, 200 mL/min | $N_2$, 200 mL/min |
| dm/dt | 0.002%/min | 0.002%/min |
| Min. dm/dt stability duration | 10 min | 10 min |
| Max. equilibrium time | 180 min | 180 min |
| RH range | ambient RH-95% RH-0% RH-30% RH ambient RH-95% RH-0% RH-95% RH | ambient RH-95% RH-0% RH-95% RH |
| RH step size | 10% RH from 0% RH to 90% RH and 90% RH to 0% RH 5% RH from 90% RH to 95% RH and 95% RH to 90% RH | 10% RH from 0% RH to 90% RH and 90% RH to 0% RH 5% RH from 90% RH to 95% RH and 95% RH to 90% RH |

DVS test was performed for Type A* family to investigate its form stability as a function of relative humidity. The DVS test was first conducted in a couple of cycles with different ends (30% and 95% RH) at 25° C. The samples were equilibrated at each RH point until wt % change was lower than 0.002% or the total time reached 3 hrs.

Figure 4:
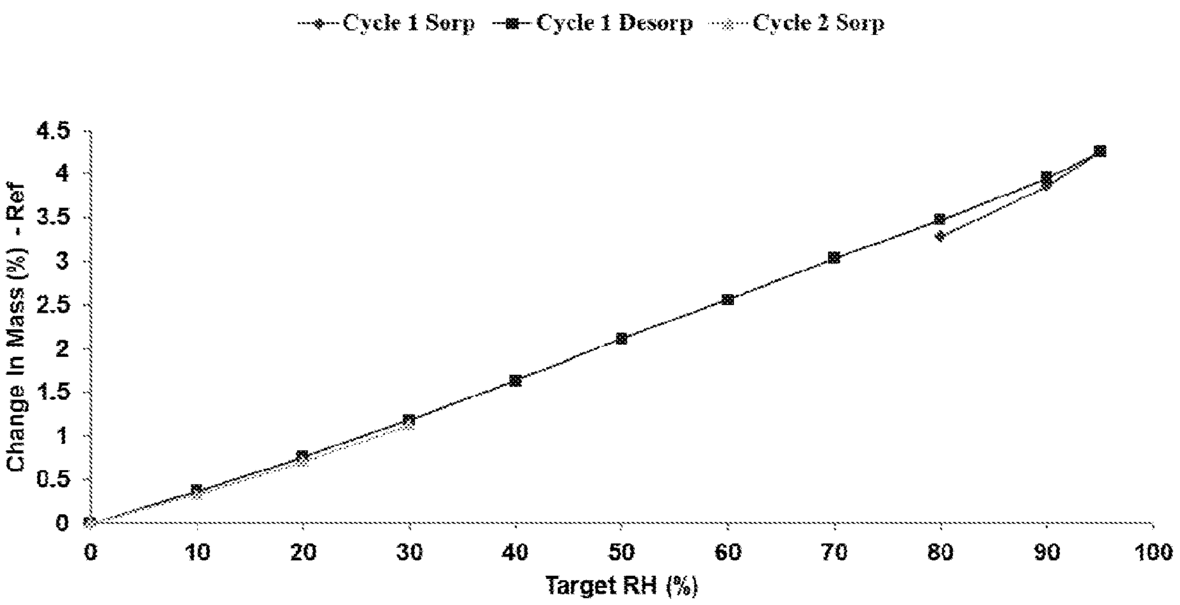
FIG. 4. Illustrates the dynamic vapor sorption (DVS) plot of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family at 25° C. (ambient RH-95% RH-0% RH-30% RH).
Figure 5:
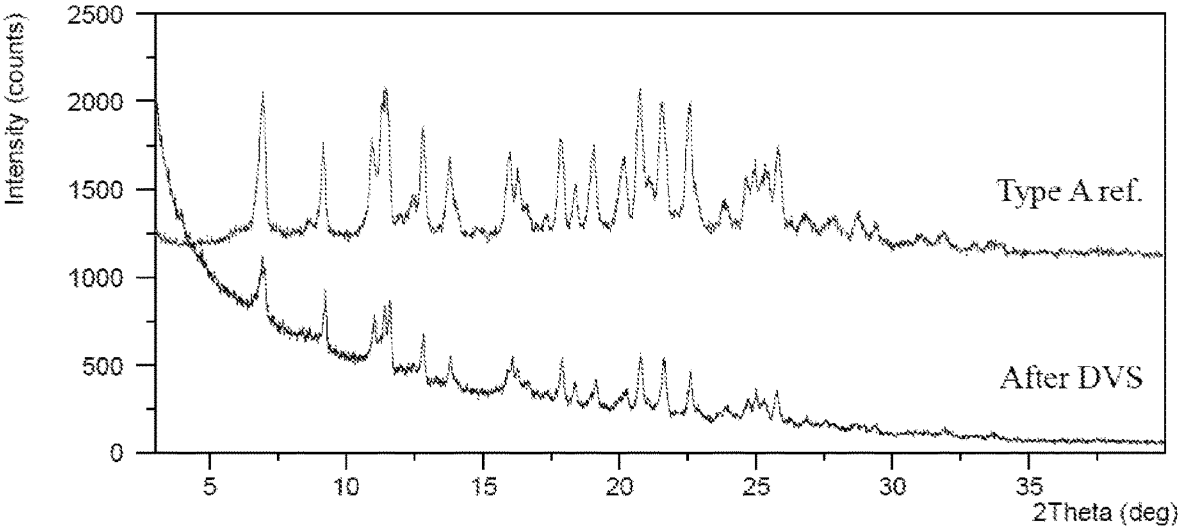
FIG. 5. Illustrates X-ray powder diffraction (XRPD) patterns of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family, before and after DVS analysis at 25° C. (ambient RH-95% RH-0% RH-30% RH) (top pattern=before DVS, bottom pattern=after DVS).
Figure 6:
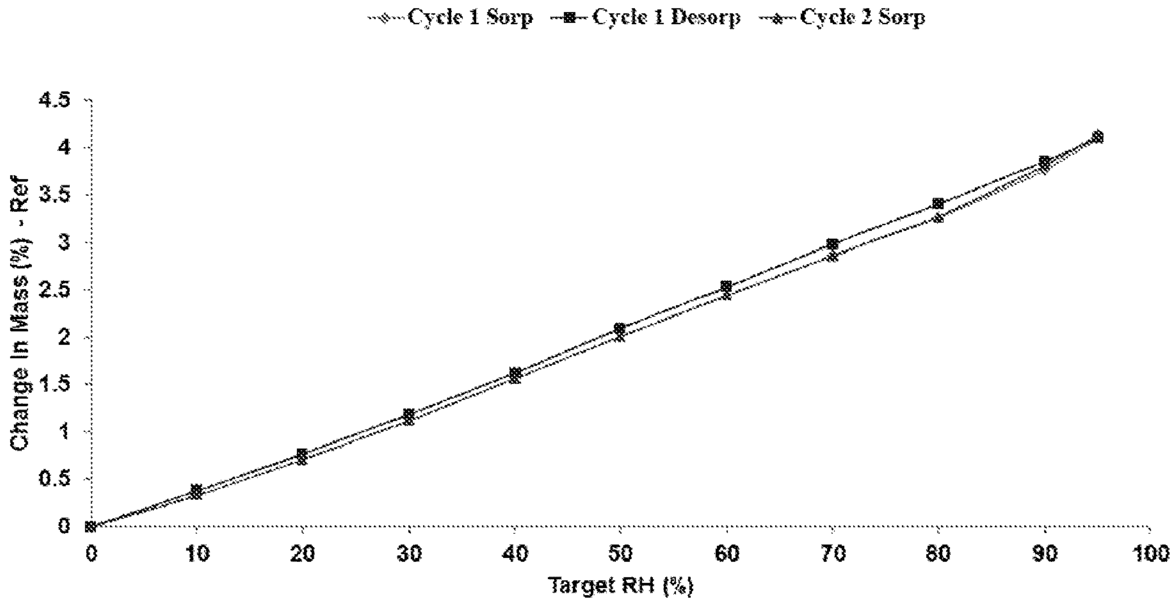
FIG. 6. Illustrates the dynamic vapor sorption (DVS) plot of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family at 25° C. (ambient RH-95% RH-0% RH-95% RH).
Figure 7:
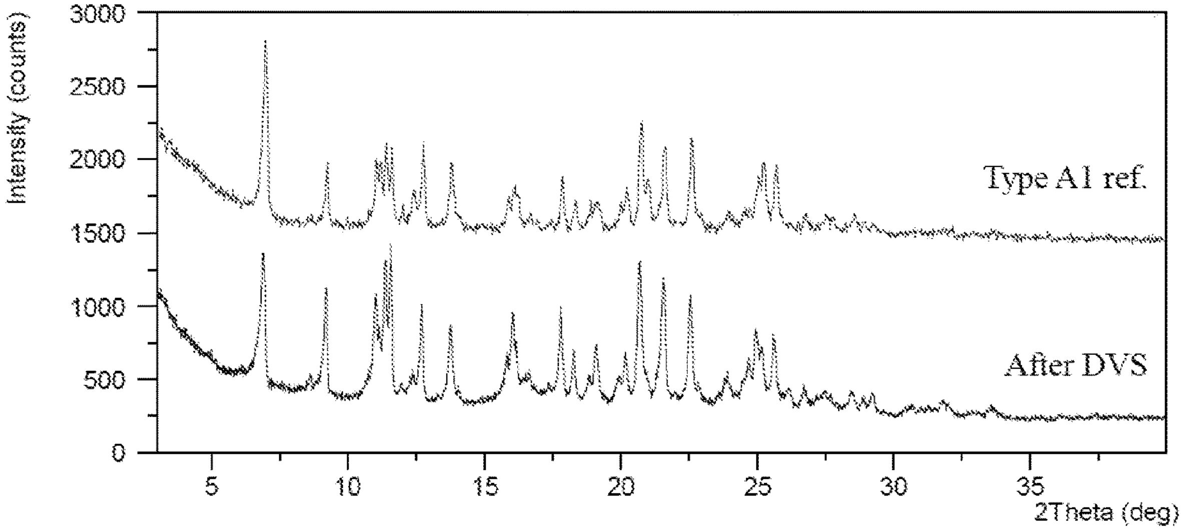
FIG. 7. Illustrates X-ray powder diffraction (XRPD) patterns of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family, before and after DVS analysis at 25° C. (ambient RH-95% RH-0% RH-95% RH) (top pattern=before DVS, bottom pattern=after DVS).

As shown in FIG. 4 and FIG. 6, the water uptake of Type A* family at 25° C. exhibited almost linear increase/decrease without history sense, which behaved similarly to a hydrate with structural voids (e.g., water channels). The crystal forms after DVS test were detected by XRPD. For the cycle (ambient RH-95% RH-0% RH-30% RH), the crystal form after DVS test was determined to be Type A (FIG. 5), corresponding to the ambient humidity (61.5% RH) when performing XRPD analysis. While for the cycle (ambient RH-95% RH-0% RH-95% RH), Type A1 was observed after DVS test (FIG. 7), corresponding to the ambient humidity (66.3% RH) when performing XRPD analysis. Based on these results, the crystal forms detected after DVS test were dependent on the ambient humidity when XRPD test was performed, which may be caused by the fast inter-conversion among Type A* family under different humidity.

Figure 8:
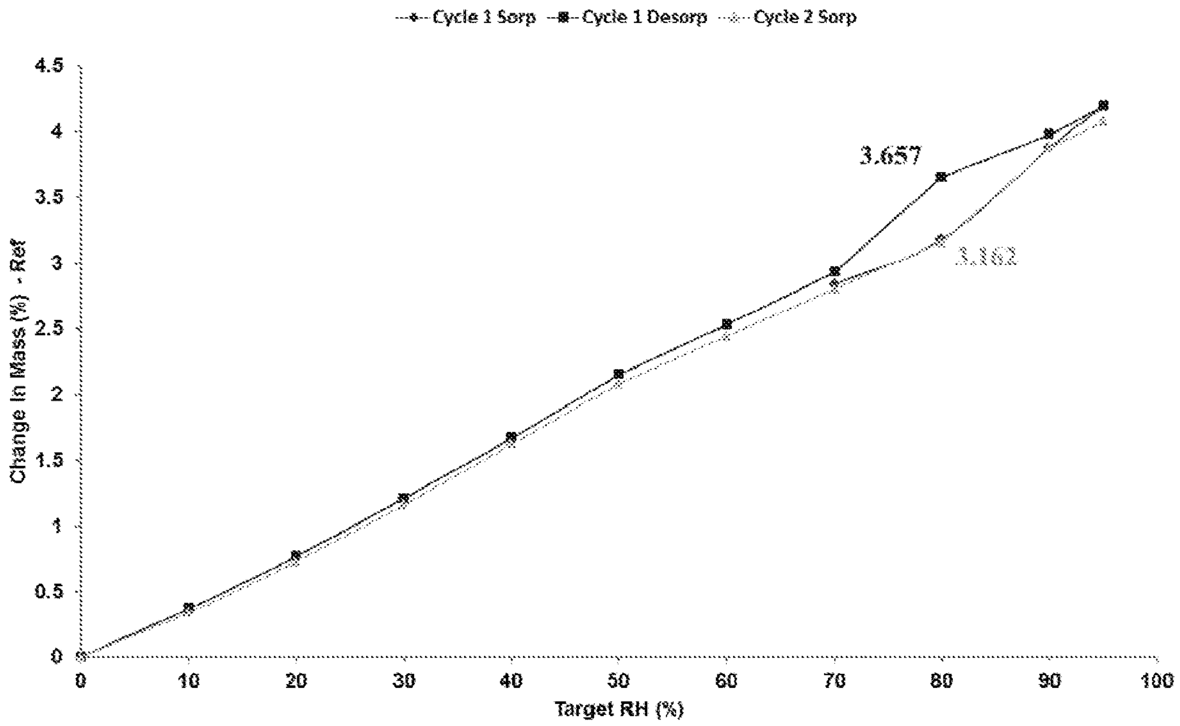
FIG. 8. Illustrates the dynamic vapor sorption (DVS) plot of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family at 40° C. (ambient RH-95% RH-0% RH-95% RH).
Figure 9:
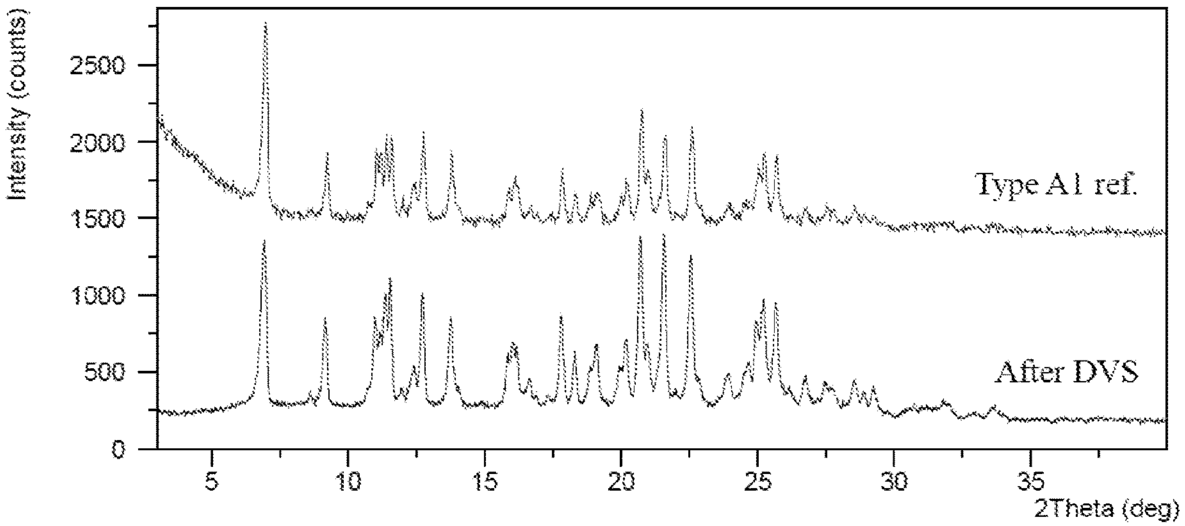
FIG. 9. Illustrates X-ray powder diffraction (XRPD) patterns of crystalline methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family, before and after DVS analysis at 40° C. (ambient RH-95% RH-0% RH-95% RH) (top pattern=before DVS, bottom pattern=after DVS).

DVS test was also conducted in the cycle (ambient RH-95% RH-0% RH-95% RH) at 40° C. The water uptake of Type A* family at 40° C. exhibited almost linear increase/decrease without history sense, except the 80% RH points presumably caused by the slower water uptake and release under the corresponding conditions (FIG. 8). The crystal form detected after DVS test was also dependent on the ambient humidity when XRPD test was performed, and Type A1 was observed in this case (69.5% RH) (FIG. 9).

Example 7: Single Crystal X-Ray Diffraction

A single crystal structure of Compound 1 Type A* family (form Type A0) was collected using crystals grown in ACN/$H_2O$ (1:3, v/v). Data were collected at 123 K using a Bruker D8 VENTURE diffractometer (Mo/Kα λ=0.71073 Å) with the following instrument parameters:

| | |
|---|---|
| X-Ray sources generator | TXS Microfocus Rotating Anode X-ray source (Mo/kα: 0.71073 Å) |
| Detector | PHOTON 100 CMOS detector (Active area: 100 × 100 mm2) |
| Goniometer | FIXED-CHI Goniometer |
| Low Temperature Devices | Cobra (Oxford Cryosystems) |
| Software package | APEX3 |

Cell parameters and an orientation matrix for data collection were retrieved and refined (least-squares refinement) by SAINT (Bruker, V8.37A, 2015) software using the setting angles of 9952 reflections in the range 2.458°<θ<23.390°. The data were collected to a maximum diffraction angle (θ) of 27.587° at 296.15. The data set was 99% complete out to 67.587° in θ, having a Mean I/σ of 11.0 and D min (Mo) of 0.77 Å.

The Compound 1 Type A* family (form Type A0) crystal system is triclinic and the space group is P1. Crystal data are summarized below:

| | |
|---|---|
| Empirical formula | C23H24F2N4O4•H2O* |
| Formula weight | 476.48 |
| Temperature | 296.15 K |
| Wavelength | Mo/$K_\alpha$(λ = 0.71073 Å) |
| Crystal system, space group | Triclinic, P1 |
| Unit cell dimensions | a = 11.440(3) Å<br>b = 14.484(3) Å<br>c = 16.358(4) Å<br>α = 113.336(6)°<br>β = 102.435(7)°<br>γ = 98.492(7)° |
| Volume | 2346.9(9) Å3 |
| Z, Calculated density | 4, 1.349 g/cm3 |
| Absorption coefficient | 0.106 |
| F(000) | 1000.0 |
| Crystal size | 0.6 × 0.2 × 0.1 |
| 2 Theta range for data collection | 4.916° to 55.174° |
| Index ranges | −14 < h < 14<br>−18 < k < 18<br>−21 < l < 21 |
| Reflections collected/Independent reflections | 87754/21252 [Rint = 0.0813, Rsigma = 0.0910] |
| Refinement method | Full-matrix least-squares on F2 |
| Completeness | 99% |
| Data/restraints/parameters | 21252/28/1250 |
| Goodness-of-fit on F2 | 1.010 |
| Final R indices [I ≥ 2sigma(I)] | R1 = 0.0707, wR2 = 0.1819 |
| Final R indices [all data] | R1 = 0.1487, wR2 = 0.2178 |
| Largest diff peak and hole | 0.57/−0.23 e.Å-3 |
| Flack parameter | 0.2(3) |

*The theoretical maxima of water incorporation would correspond to a monohydrate from the single crystal data. The actual stoichiometry of water: API in Type A* family crystals may be less than 1:1 as the water molecules in the crystal lattice exhibited disorder.

Figure 10:
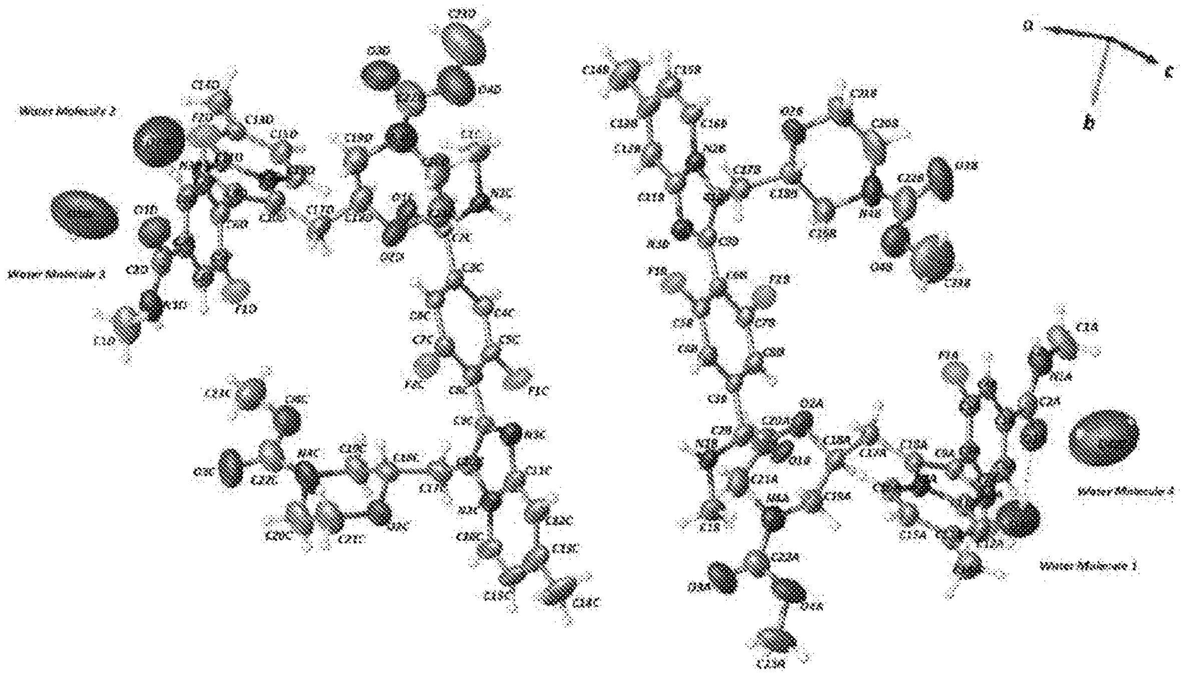
FIG. 10. Illustrates the asymmetric unit of methyl (S)-2-((2-(2,6-difluoro-4-(methylcarbamoyl)phenyl)-7-methylimidazo[1,2-a]pyridin-3-yl)methyl)morpholine-4-carboxylate (Compound 1), Type A* family, single crystal structure.
Figure 11:
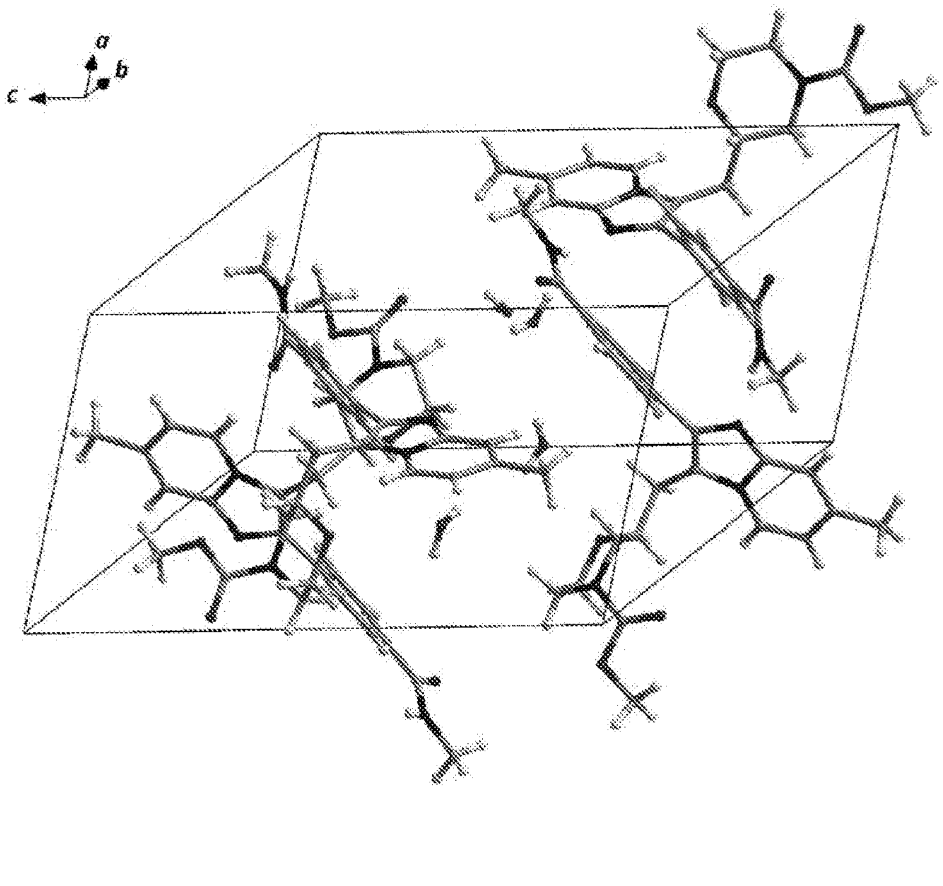
FIG. 11. Illustrates the unit cell of methyl-2-((2-(2,6-difluoro-4-(methylcarbamoyl)phenyl)-7-methylimidazo[1,2-a]pyridin-3-yl)methyl)morpholine-4-carboxylate (Compound 1), Type A* family, single crystal structure.

The asymmetric unit of Type A* family single crystal structure is composed of four API molecules (crystallographic-independent conformers) and theoretically four water molecules, which indicates that the single crystal is a hydrate (FIG. 10). The unit cell of the single crystal is shown in FIG. 11.

From the single crystal structure, there are four possible hydration sites in the unit cell. If each of the hydration sites is occupied by one water molecule, a monohydrate would be expected, which should correspond to the theoretical maxima water incorporation in the crystal lattice of Type A* family crystals. For a monohydrate, if only lattice waters are considered, the theoretical maxima water uptake is 3.9%, which is very close to the experimental DVS results (~4.1-4.2% at 100% RH at 25° C.). In addition, there may be less than one water molecule on each hydration site because of the disorder, and a stoichiometry of less than 1:1 for water: API may be expected in an actual Type A* family crystal which is consistent with the almost linear increase/decrease of water content as a function of humidity in the DVS test.

We claim:

1. A crystalline form of methyl (S)-2-((2-(2,6-difluoro-4-(methylcarbamoyl)phenyl)-7-methylimidazo[1,2-a]pyridin-3-yl)methyl)morpholine-4-carboxylate, or solvate thereof, wherein the crystalline form has an X-ray powder diffraction (XRPD) pattern with characteristic peaks at about 6.9° 2-Theta, 11.3° 2-Theta, 11.5° 2-Theta, 12.8° 2-Theta, 17.8° 2-Theta, 20.7° 2-Theta, 21.6° 2-Theta, and 22.6° 2-Theta.

2. The crystalline form of claim 1, wherein the crystalline form is obtained from acetonitrile, acetone, tert-butyl methyl ether, water, methanol, ethanol, isopropanol, propanol, butanol, diethyleneglycol, ethyl acetate, isopropyl acetate, tetrahydrofuran, 2-methyltetrahydrofuran, dimethylsulfoxide, dimethylformamide, methyl ethyl ketone, methyl isobutyl ketone, butyl acetate, hexane, heptane, dichloromethane, chloroform, 1,2-dichloroethane, dimethoxyethane, toluene, anisole, or combinations thereof.

3. A pharmaceutical composition comprising the crystalline form of claim 1, and at least one inactive ingredient selected from pharmaceutically acceptable carriers, diluents, and excipients.

4. The crystalline form of claim 1, wherein the crystalline form is obtained from acetonitrile, acetone, tert-butyl methyl ether, water, methanol, ethanol, isopropanol, propanol, butanol, diethyleneglycol, isopropyl acetate, tetrahydrofuran, 2-methyltetrahydrofuran, dimethylsulfoxide, dimethylformamide, methyl ethyl ketone, methyl isobutyl ketone, butyl acetate, hexane, heptane, dichloromethane, chloroform, 1,2-dichloroethane, dimethoxyethane, toluene, anisole, or combinations thereof.

* * * * *